(12) United States Patent
Barnham et al.

(10) Patent No.: US 8,389,506 B2
(45) Date of Patent: Mar. 5, 2013

(54) COMPOUNDS FOR THERAPY AND DIAGNOSIS

(75) Inventors: Kevin Jeffrey Barnham, Coburg (AU); Vijaya Kenche, Oakleigh East (AU)

(73) Assignee: Prana Biotechnology Ltd., Parkville (AU)

( * ) Notice: Subject to any disclaimer, the term of this patent is extended or adjusted under 35 U.S.C. 154(b) by 228 days.

(21) Appl. No.: 12/746,382

(22) PCT Filed: Dec. 5, 2008

(86) PCT No.: PCT/AU2008/001802
§ 371 (c)(1), (2), (4) Date: Nov. 30, 2010

(87) PCT Pub. No.: WO2009/070847
PCT Pub. Date: Jun. 11, 2009

(65) Prior Publication Data
US 2011/0110850 A1 May 12, 2011

(30) Foreign Application Priority Data
Dec. 7, 2007 (AU) .............................. 2007906668

(51) Int. Cl.
*A61K 31/555* (2006.01)
*C07F 15/00* (2006.01)
(52) U.S. Cl. ......................... 514/187; 546/10
(58) Field of Classification Search ................ 514/187; 546/10
See application file for complete search history.

(56) References Cited

U.S. PATENT DOCUMENTS

| | | | |
|---|---|---|---|
| 4,946,954 A | 8/1990 | Talebian et al. | |
| 4,956,459 A | 9/1990 | Talebian et al. | |
| 5,026,694 A | 6/1991 | Skov et al. | |
| 5,091,521 A | 2/1992 | Kolar et al. | |
| 5,451,576 A | 9/1995 | Sessler et al. | |
| 5,547,982 A | 8/1996 | Abrams et al. | |
| 5,648,384 A | 7/1997 | Kidani et al. | |
| 6,417,178 B1 | 7/2002 | Klunk et al. | |
| 6,664,111 B2 | 12/2003 | Bentsen et al. | |
| 7,074,308 B2 | 7/2006 | Mao et al. | |
| 7,166,733 B2 | 1/2007 | Nowotnik et al. | |
| 7,183,072 B1 | 2/2007 | Hainfeld | |
| 7,205,287 B2 | 4/2007 | Bartoli et al. | |
| 7,208,611 B2 | 4/2007 | Gao et al. | |
| 2004/0175387 A1 | 9/2004 | Sood et al. | |

FOREIGN PATENT DOCUMENTS

WO 97/41856 A1 11/1997
WO 01/07442 A1 2/2001

OTHER PUBLICATIONS

Massacesi, M.: Cobalt and Nickel chloride and bromide complexes of 2-(2'-methyl-8'-quinolyl) benzoxazole and 2-(2' or 4'-methyl 8'-quinolyl) benzimidazole. Transition Met. Chem., vol. 11, pp. 102-106, 1986.*

Bachand, Benoit et al., "Formal Transfers of Hydride from Carbon-Hydrogen Bonds. Attempts Generation of Molecule Mydrogen by Intramolecular Reduction of Protons Bound by 2,3-Dihydro-1,3-dimethyl-2-(8-quinolinyl)-1H-benzimidazole," J. Org. Chem., vol. 52:5443-5446 (1987).

Gumus, F. et al., "Synthesis, characterization and in vitro cytotoxic, mutagenic and antimicrobial activity of platinum(II) complexes with substituted benzimidazole ligands," Journal of Inorganic Biochemistry, vol. 94:255-262 (2003).

He, Xiao-Feng et al., "Pyridyl benzimidazole, benzoxazole, and benzothiazole platinum complexes," Polyhedron, vol. 23:155-160 (2004).

(Continued)

*Primary Examiner* — Charanjit Aulakh
(74) *Attorney, Agent, or Firm* — Nelson Mullins Riley & Scarborough; Amy E. Mandragouras, Esq.; Pankaj N. Desai

(57) ABSTRACT

The present invention relates to a transition metal complex represented by Formula (I) or salts thereof, or to a ligand represented by Formula (H) or salts thereof, wherein X represents a transition metal, preferably Pt, and methods for their use and preparation. In particular, the invention relates to compounds which may possess useful therapeutic activity in treating amyloid diseases, and in particular, Alzheimer's disease. The invention also relates to the use of these compounds in methods of therapy, and diagnosis, and the manufacture of medicaments as well as compositions containing these compounds.

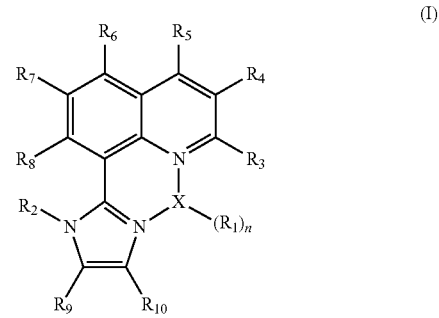

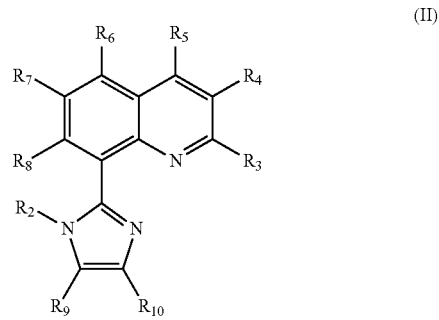

29 Claims, 19 Drawing Sheets

OTHER PUBLICATIONS

Margiotta, Nicola et al., "Sterically hindered complexes of platinum(II) with planar heterocyclic nitrogen donors. A novel complex with 1-methyl-cytosine has a spectrum of activity different from cisplatin and is able of overcoming acquired cisplatin resistance," Journal of Inorganic Biochemistry, vol. 100:1849-1857 (2006).

Mock, Christian et al., "Novel Pt(II) anticancer agents and their Pd(II) analogues: synthesis, crystal structures, reactions with nucleobases and cytotoxicities," Inorganica Chimica Acta, vol. 319:109-116 (2001).

Shavaleev, Nail M. et al., "Complexes of substituted derivatives of 2-(2-pyridyl)benzimidazole with Re(I), Ru(II) and Pt(II): structures, redox and luminescence properties," Dalton Trans., pp. 3678-3688 (2004).

Metallocomplex provisionials: Overview and search results dated Jun. 22, 2007.

Novelty Search Report dated Sep. 11, 2007.

STN Search Report for Angular Series Substructure Search dated Sep. 5, 2007.

International Search Report for Application No. PCT/AU2008/001802, dated Jan. 26, 2009.

* cited by examiner

- Graph line beginning at 200 mAu is Example 9
- Graph line beginning at 400 mAu is Example 11 (the precursor to Example 9).
- Graph line beginning at 800 mAu is a mixture of Examples 9 and 11, indicating the ability to separate each compound when as a mixture.

Scale bars 100nm

* EM imaging of these sections was difficult with regard to focusing; indicative of monomeric peptide stuck to grids Ref: Chi

COMPOUNDS FOR THERAPY AND DIAGNOSIS

RELATED APPLICATIONS

This application is a 35 U.S.C. §371 filing of International Application Number PCT/AU2008/001802 which was filed on Dec. 5, 2008, which claims priority to Australian Application 2007906668, which was filed on Dec. 7, 2007. The entire contents of the aforementioned applications are hereby incorporated herein by reference.

FIELD OF THE INVENTION

The present invention relates generally to chemical compounds and methods for their use and preparation. In particular, the invention relates to chemical compounds which may possess useful therapeutic activity in treating amyloid diseases, and in particular, Alzheimer's disease. The invention also relates to the use of these compounds in methods of therapy, and diagnosis of amyloid diseases, and the manufacture of medicaments as well as compositions containing these compounds.

BACKGROUND OF THE INVENTION

Amyloidosis is a general term that describes a number of diseases characterised by extracellular deposition of protein fibrils which form numerous 'amyloid deposits'. These plaque-like deposits may occur in localised sites, such as the brain or systemically. The fibrillar composition of these deposits is an identifying characteristic for the various forms of amyloid disease. The following diseases and their associated protein have been identified as amyloid diseases: Diabetes mellitus type 2 (amylin); Alzheimer's disease (Aβ 39-42); Parkinson's disease (alpha-synuclein); Huntington's disease (huntingtin); Creutzfeldt-Jakob disease (PrP in cerebrum); congestive heart failure (PrP or transthyretin) and Bovine spongiform encephalopathy (PrP). Due to recent reports, Age related Macular Degeneration, 'AMD', is a further condition which may be characterized by amyloid deposits.

Alzheimer's disease (AD) is the most common cause of progressive dementia in the elderly population. AD is characterised by the presence of distinctive lesions in the patient's brain. These brain lesions include abnormal intracellular filaments called neurofibrillary tangles, and extracellular deposits of amyloid plaques. Amyloid deposits are also present in the walls of cerebral blood vessels of Alzheimer's patients. The major constituent of amyloid plaques has been identified as a 4 kilodalton peptide (39-43 residues) called beta-amyloid peptide ('Abets' or 'Aβ'). Alzheimer's disease brain tissue is characterised by Abeta plaques and observations suggest that Abeta deposition contributes to the destruction of neurons. Abeta has been shown to be toxic to mature neurons both in culture and in vivo.

Currently, there is no medication capable of curing or stopping the progression of any amyloid diseases, including AD. Therapies for AD such as inhibition of acetylcholinesterase (AchE)[2] activity and antagonisism of N-methyl-D-aspatarte (NMDA) receptors produce only modest symptomatic improvements in some patients. Other therapeutic approaches currently in clinical development aim to control the levels of Aβ amyloid in the brain, either by immunization or through pharmacological manipulation. Drugs that target BACE and γ-secretase, the two enzymes responsible for Aβ production have concern due to side-effects of secretase inhibition since these enzymes are not specific and process a variety of substrates including the NOTCH protein.

It has been reported that the aggregated Abeta peptide has redox properties and can generate reactive oxygen species, which attack enzymes and possibly cell membranes, causing neurotoxicity and brain cell death. It has also been reported that the coordination of metal ions such as copper and zinc accelerates ABeta aggregation and generates reactive oxygen species and hydrogen peroxide. Studies have shown that a range of commonly available metal chelators (TPEN, EGTA and bathcuproine) with a reasonable affinity for Cu, Zn and Fe can solubilize deposited ABeta from post-mortem brain tissue. A potential limiting factor is that treatment with metal chelators is by definition non-specific. While limits on metal-binding affinities and tissue selectivity reduce the effects of this non-selectivity, the metal ions targeted are ubiquitous and essential and there are inherent risks associated with their non-discriminate removal.

The cure or disruption of amyloid diseases, particularly Alzheimer's disease, is further withheld by a lack of accurate and usable imaging and patient diagnostic techniques. For example, whilst data emerging from a range of $^{11}$C-PIB studies demonstrates quantitative determination of brain Abeta non-invasively, therefore allowing monitoring of potential anti-amyloid therapeutic agents, the very short half-life of $^{11}$C, precludes widespread application of $^{11}$C-PIB in a relevant fashion in clinical settings. $^{11}$C-PIB requires not only a very expensive PET scanner (cost ~$2M) but also an in situ cyclotron (cost ~$2M) for the production of the radio-isotope [11]C. The high production costs therefore preclude $^{11}$C-PIB PET scanning from having a public health impact as a widespread screening test.

Accordingly, as well as providing therapeutics for treating amyloid diseases there is also a need for new imaging agents that target the underlying pathogenic mechanisms in amyloidosis type diseases, particularly AD, for early diagnosis of such disease states.

The present inventors have developed novel metallocomplexes that act as preoccupants or blockers of metal binding sites on amyloid proteins.

SUMMARY OF THE INVENTION

Accordingly, the present invention provides transition metal complex of formula (I) or salts thereof:

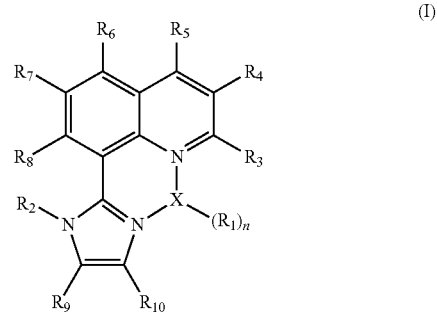

wherein:
X is selected from a transitional metal consisting of Pt, Tc, Pd, Mn, Fe, Ru, Au, Re and Rh;
n is an integer from 2 to 6;
each $R_1$ is independently selected from halogen, NR'R''R''' (where each of R', R'', and R''' is independently selected from hydrogen, alkyl, cycloalkyl, aryl, heteroaryl, heterocycyl and oxyacyl), optionally substituted acyloxy, optionally substituted alkoxy, SR'R" (where each of R' and R" is independently selected from hydrogen, alkyl, cycloalkyl, aryl, heteroaryl, heterocycyl and oxyacyl), optionally substituted heteroaryl, optionally substituted carbohydrate, or any two $R_1$ form a malonate, oxalate or glycolate;

$R_2$ is selected from H, optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and wherein each $R_3$-$R_{10}$ independently represents H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or $R_9$ and $R_{10}$ together form an optionally substituted aryl, optionally substituted heteroaryl, or optionally substituted cycloalkenyl.

The present invention also provides a method for treating an amyloid disorder including the step of administering to a patient in need thereof a transition metal complex of formula (I) or a pharmaceutically acceptable salt thereof;

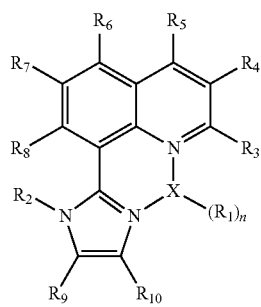

(I)

wherein:

X is selected from a transition metal consisting of Pt, Tc, Pd, Mn, Fe, Co, Ni, Ru, Cd, Au, Re, Rh and Hg;

n is an integer from 2 to 6;

each $R_1$ is independently selected from halogen, NR'R"R'" (where each of R', R", and R'" is independently selected from hydrogen, alkyl, cycloalkyl, aryl, heteroaryl, heterocycyl and oxyacyl), optionally substituted acyloxy, optionally substituted alkoxy, SR'R" (where each of R' and R" is independently selected from hydrogen, alkyl, cycloalkyl, aryl, heteroaryl, heterocycyl and oxyacyl), optionally substituted heteroaryl, optionally substituted carbohydrate, or any two $R_1$ form a malonate, oxalate or glycolate;

$R_2$ is selected from H, optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and wherein each $R_3$-$R_{10}$ independently represents H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or $R_9$ and $R_{10}$ together form an optionally substituted aryl, optionally substituted heteroaryl, or optionally substituted cycloalkenyl.

The present invention also provides the use of a transition metal complex of formula (I) or a salt thereof:

wherein:
- X is selected from a transition metal consisting of Pt, Tc, Pd, Mn, Fe, Co, Ni, Ru, Cd, Au, Re, Rh and Hg;
- n is an integer from 2 to 6;
- each $R_1$ is independently selected from halogen, NR'R"R'" (where each of R', R", and R'" is independently selected from hydrogen, alkyl, cycloalkyl, aryl, heteroaryl, heterocycyl and oxyacyl), optionally substituted acyloxy, optionally substituted alkoxy, SR'R" (where each of R' and R" is independently selected from hydrogen, alkyl, cycloalkyl, aryl, heteroaryl, heterocycyl and oxyacyl), optionally substituted heteroaryl, optionally substituted carbohydrate, or any two $R_1$ form a malonate, oxalate or glycolate;
- $R_2$ is selected from H, optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and
- wherein each $R_3$-$R_{10}$ independently represents H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or $R_9$ and $R_{10}$ together form an optionally substituted aryl, optionally substituted heteroaryl, or optionally substituted cycloalkenyl.

in the manufacture of a medicament for treating an amyloid disorder.

Furthermore, the invention also provides a method of diagnosing an amyloid disorder comprising:
(i) administering a detectable quantity of a transition metal complex of formula (I) or a salt thereof to a patient;

wherein:
- X is selected from a transition metal consisting of Pt, Tc, Pd, Mn, Fe, Co, Ni, Ru, Cd, Au, Re, Rh and Hg;
- n is an integer from 2 to 6;
- each $R_1$ is independently selected from halogen, NR'R"R'" (where each of R', R", and R'" is independently selected from hydrogen, alkyl, cycloalkyl, aryl, heteroaryl, heterocycyl and oxyacyl), optionally substituted acyloxy, optionally substituted alkoxy, SR'R" (where each of R' and R" is independently selected from hydrogen, alkyl, cycloalkyl, aryl, heteroaryl, heterocycyl and oxyacyl), optionally substituted heteroaryl, optionally substituted carbohydrate, or any two $R_1$ form a malonate, oxalate or glycolate;
- $R_2$ is selected from H, optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and
- wherein each $R^3$-$R^{10}$ independently represents H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or $R_9$ and $R_{10}$ together form an optionally substituted aryl, optionally substituted heteroaryl, or optionally substituted cycloalkenyl; and (ii) detecting the binding of the transition metal complex to an amyloid deposit in said patient;

wherein one of $R_1$-$R_{10}$ or a substituent of an aryl, heteroaryl, or cycloalkenyl group when $R_9$ and $R_{10}$ together form a substituted aryl, substituted heteroaryl, or substituted cycloalkenyl is or comprises the group consisting of $^{131}I$, $^{123}I$, $^{76}Br$, $^{75}Br$, $^{18}F$, $^{19}F$, or a fluorescent moiety.

DETAILED DESCRIPTION OF THE INVENTION

Figure 1:
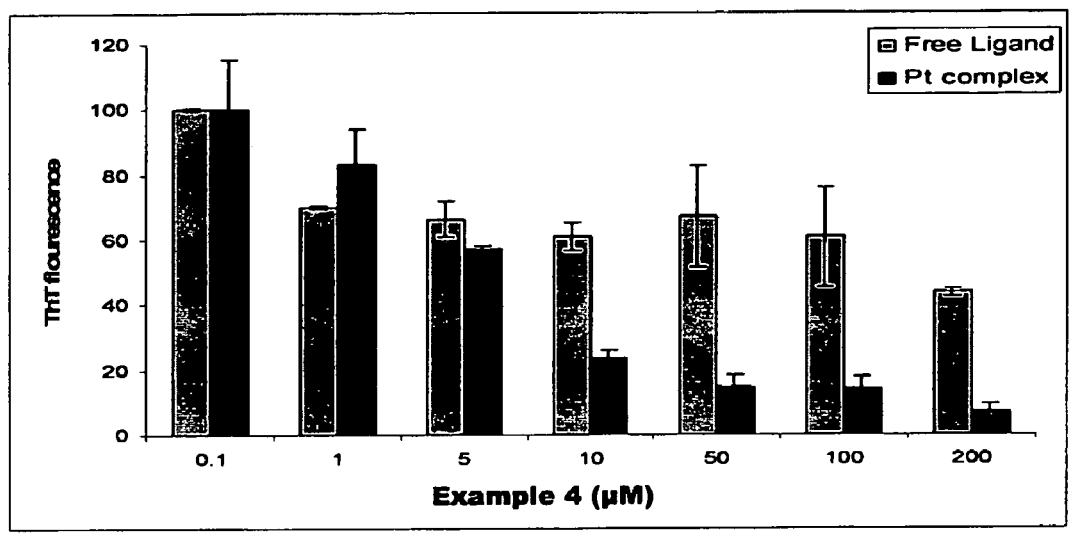
FIG. 1 is a bar graph showing the inhibition of amyloid formation by test compound Example 4 in free-ligand and metal complex form, over a concentration range. Data is presented as fluorescence units.

The invention is based on the discovery that the transition metal complexes of the general formula I, as described in the above Summary of the Invention may interact with the metal binding site of an amyloid protein, thereby altering the protein conformation and function. Such complexes have significant potential for the treatment of a variety of disorders characterised by amyloid formation, herein referred to as "amyloid disorders", and in particular Alzheimer's disease and related conditions.

"Alkyl" refers to monovalent alkyl groups which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like.

"Alkylene" refers to divalent alkyl groups preferably having from 1 to 10 carbon atoms and more preferably 1 to 6 carbon atoms. Examples of such alkylene groups include methylene (—CH$_2$—), ethylene (—CH$_2$CH$_2$—), and the propylene isomers (e.g., —CH$_2$CH$_2$CH$_2$— and —CH(CH$_3$)CH$_2$—), and the like.

"Aryl" refers to an unsaturated aromatic carbocyclic group having a single ring (eg. phenyl) or multiple condensed rings (eg. naphthyl or anthryl), preferably having from 6 to 14 carbon atoms. Examples of aryl groups include phenyl, naphthyl and the like.

"Arylene" refers to a divalent aryl group wherein the aryl group is as described above.

"Aryloxy" refers to the group aryl-O— wherein the aryl group is as described above.

"Arylalkyl" refers to-alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH═CH$_2$), n-propenyl (—CH$_2$CH═CH$_2$), iso-propenyl (—C(CH$_3$)═CH$_2$), but-2-enyl (—CH$_2$CH═CHCH$_3$), and the like.

"Alkenyloxy" refers to the group alkenyl-O— wherein the alkenyl group is as described above.

"Alkenylene" refers to divalent alkenyl groups preferably having from 2 to 8 carbon atoms and more preferably 2 to 6 carbon atoms. Examples include ethenylene (—CH═CH—), and the propenylene isomers (e.g., —CH$_2$CH═CH— and —C(CH$_3$)═CH—), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH—), propargyl (—CH$_2$C≡CH), pent-2-ynyl (—CH$_2$C≡CCH$_2$—CH$_3$), and the like.

"Alkynyloxy" refers to the group alkynyl-O— wherein the alkynyl groups are as described above.

"Alkynylene" refers to the divalent alkynyl groups preferably having from 2 to 8 carbon atoms and more preferably 2 to 6 carbon atoms. Examples include ethynylene (—C≡C—), propynylene (—CH$_2$—C≡C—), and the like.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Amino" refers to the group —NR"R" where each R" is independently hydrogen, alkyl, cycloalkyl, aryl, heteroaryl, and heterocyclyl and where of alkyl, cycloalkyl, aryl, heteroaryl and heterocyclyl is as described herein.

"Aminoacyl" refers to the group —C(O)NR"R" where each R" is independently hydrogen, alkyl, cycloalkyl, aryl, heteroaryl, and heterocyclyl and where of alkyl, cycloalkyl, aryl, heteroaryl and heterocyclyl is as described herein.

"Acylamino" refers to the group —NR"C(O)R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acyloxy" refers to the groups —OC(O)-alkyl, —OC(O)-aryl, —C(O)O-heteroaryl, and —C(O)O-heterocyclyl where alkyl, aryl, heteroaryl and heterocyclyl are as described herein.

"Aminoacyloxy" refers to the groups —OC(O )NR"-alkyl, —OC(O)NR"-aryl, —OC(O)NR"-heteroaryl, and —OC(O)NR"-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR"C(O)O-alkyl, —NR"C(O)O-aryl, —NR"C(O)O-heteroaryl, and NR"C(O)O-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O-heteroaryl, and —OC(O)O-heterocyclyl where alkyl, cycloalkyl, aryl, heteroaryl, and heterocyclyl are as described herein.

"Acylimino" refers to the groups —C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR")—OR" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 11 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, indanyl, 1,2,3,4-tetrahydronapthalenyl and the like.

"Cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

"Halo" or "halogen" refers to fluoro, chloro, bromo and iodo.

"Heteroaryl" refers to a monovalent aromatic heterocyclic group which fulfils the Hückel criteria for aromaticity (ie. contains 4n+2π electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg. pyridyl, pyrrolyl or N-oxides thereof or furyl) or multiple condensed rings (eg. indolizinyl, benzoimidazolyl, coumarinyl, quinolinyl, isoquinolinyl or benzothienyl). It will be understood that where, for instance, R$_2$ or R' is an optionally substituted heteroaryl which has one or more ring heteroatoms, the heteroaryl group can be connected to the core molecule of the compounds of the present invention, through a C—C or C-heteroatom bond, in particular a C—N bond.

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatom is nitrogen. It will be understood that where, for instance, R$_2$ or R' is an optionally substituted heterocyclyl which has one or more ring heteroatoms, the heterocyclyl group can be connected to the core molecule of the compounds of the present invention, through a C—C or C-heteroatom bond, in particular a C—N bond.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Heteroarylene" refers to a divalent heteroaryl group wherein the heteroaryl group is as described above.

"Heterocyclylene" refers to a divalent heterocyclyl group wherein the heterocyclyl group is as described above.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylamino" refers to the groups —NR"—P(O)(R''')(OR'''') where R" represents H, alkyl, cycloalkyl, alkenyl, or aryl, R''' represents OR'''' or is hydroxy or amino and R'''' is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR"—, alkyl-S(O)—NR"—, cycloalkyl-S(O)—NR"—, aryl-S(O)—NR"—, heteroaryl-S(O)—NR"—, and heterocyclyl-S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR"—, alkyl-S(O)$_2$—NR"—, cycloalkyl-S(O)$_2$—NR"—, aryl-S(O)$_2$—NR"—, heteroaryl-S(O)$_2$—NR"—, and heterocyclyl-S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR"—, alkylO—S(O)—NR"—, cycloalkylO—S(O)—NR"—, arylO—S(O)—NR"—, heteroarylO—S(O)—NR"—, and heterocyclylO—S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfonylamino" refers to groups HO—S(O)$_2$—NR"—, alkylO—S(O)$_2$—NR"—, cycloalkylO—S(O)$_2$—NR"—, arylO—S(O)$_2$—NR"—, heteroarylO—S(O)$_2$—NR"—, and heterocyclylO—S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R"R"N—C(S)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR"—, alkyl-C(S)—NR"—, cycloalkyl-C(S)—NR"—, aryl-C(S)—NR"—, heteroaryl-C(S)—NR"—, and heterocyclyl-C(S)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R"R"N—S(O)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R"R"N—S(O)$_2$—, where each R" is independently hydrogen, alkyl, cycloalkyl, aryl, heteroaryl, and heterocyclic and where each of alkyl, cycloalkyl, aryl, heteroaryl and heterocyclyl is as described herein.

In this specification "optionally substituted" is taken to mean that a group may or may not be further substituted or fused (so as to form a condensed polycyclic group) with one or more groups selected from hydroxyl, acyl, alkyl, alkoxy, alkenyl, alkenyloxy, alkynyl, alkynyloxy, amino, aminoacyl, thio, arylalkyl, arylalkoxy, aryl, aryloxy, carboxyl, acylamino, cyano, halogen, nitro, phosphono, sulfo, phosphorylamino, phosphinyl, heteroaryl, heteroaryloxy, heterocyclyl, heterocyclyloxy, oxyacyl, oxime, oxime ether, hydrazone, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like, and may also include a bond to a solid support material, (for example, substituted onto a polymer resin). For instance, an "optionally substituted amino" group may include amino acid and peptide residues. In the case of optionally substituted alkoxy, the term "optionally substituted" may indicate that one or more saturated carbon atoms may be substituted for a heteroatom or heterogroup such as O, S, NH and the like. For example an optionally substituted alkoxy group could be represented by a group such as —O—CH$_2$CH$_2$—O—CH$_2$CH$_2$OH or polyethyleneglycols of other lengths.

In an embodiment one or two of $R_3$-$R_{10}$ are substituted (i.e., other than hydrogen).

In a further preferred embodiment $R_9$ and $R_{10}$ together form an optionally substituted aryl group. More preferably $R_9$ and $R_{10}$ together form an optionally substituted phenyl group. Accordingly, in a preferred embodiment the invention provides a transition metal complex of formula (I') or a salt thereof;

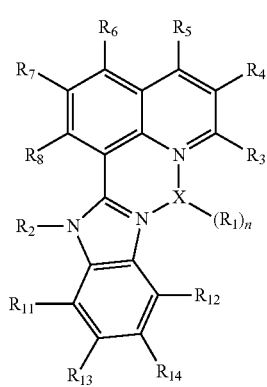

wherein:
X is selected from a transition metal consisting of Pt, Tc, Pd, Mn, Fe, Ru, Au, Re and Rh;
n is an integer from 2 to 6;
each $R_1$ is independently selected from halogen, NR'R"R'" (where each of R', R", and R'" is independently selected from hydrogen, alkyl, cycloalkyl, aryl, heteroaryl, heterocycyl and oxyacyl), optionally substituted acyloxy, optionally substituted alkoxy, SR'R" (where each of R' and R" is independently selected from hydrogen, alkyl, cycloalkyl, aryl, heteroaryl, heterocycyl and oxyacyl), optionally substituted heteroaryl, optionally substituted carbohydrate, or any two $R_1$ form a malonate, oxalate or glycolate;
$R_2$ is selected from H, optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and
wherein each $R_3$-$R_8$, and $R_{11}$-$R_{14}$ independently represent H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy.

In an embodiment one or two of $R_3$-$R_8$ and $R_{11}$-$R_{14}$ of compounds of formula (I') are substituted.

In a further embodiment one of $R_3$-$R_8$ and $R_{11}$-$R_{14}$ of compounds of formula (I') is substituted.

In a further embodiment variables $R_3$-$R_8$ and $R_{11}$-$R_{14}$ in compounds of formula (I') represent hydrogen.

When present, the substituents for $R_3$-$R_{14}$ in compounds of formulae (I) and (I') may be selected from:
substituted aryl group, preferably halophenyl, aminophenyl, carboxyphenyl, hydroxyphenyl, cyanophenyl, nitrophenyl, trihaloalkylphenyl, and alkylphenyl.
acyl group, preferably formyl acetyl, propionyl, benzoyl (optionally substituted with methyl, methoxy, halogen, nitro, trifluoromethyl or cyano);
alkoxy group, preferably methoxy and ethoxy;
substituted alkoxy group, preferably a carbohydrate residue;
oxyacyl group, preferably methoxycarbonyl, ethoxycarbonyl, propoxycarbonyl, butyloxycarbonyl, isobutyloxycarbonyl;
acyloxy group, preferably acetoxy and propioxy;
substituted arylalkyl group, preferably 1-hydroxybenzyl, and 1-thiobenzyl;
sulfinyl group, preferably methylsulfinyl, ethylsulfinyl, benzene sulfinyl (optionally substituted with methyl, methoxy, halogen, nitro, trifluoromethane or cyano), methoxysulfinyl, ethoxysulfinyl;
sulfonyl group, preferably methylsulfonyl, ethylsulfonyl, benzenesulfonyl (optionally substituted with methyl, methoxy, halogen, nitro, trifluoromethane or cyano), methoxycarbo, trifluoromethane;
oxyacylamino group, preferably methoxycarbonylamido, and ethoxycarbonyl amido;
oxythioacyl group, preferably methoxythiocarbonyl and ethoxythiocarbonyl;
thioacyloxy group, preferably thionoacetoxy and thionopropionoxy;
sulphinylamino group, preferably methylsulfinylamino, ethylsulfinylamino, and benzenesulfinylamino (optionally substituted with methyl, methoxy, halogen, nitro, trifluoromethane or cyano);
amino group, preferably N-methylamino, and N,N'-dimethylamino;
substituted amino groups, preferably residues of L-valine, D-valine, L-alanine, D-alanine, aspartic acid, and alanylserine;
sulphonylamino group, preferably methylsulfonylamino, ethylsulfonylamino and benzene sulfonylamino (optionally substituted with methyl, methoxy, halogen, nitro, trifluoromethane or cyano);
substituted thio group, preferably alkylthio;

oxysulfinylamino group, preferably methoxysulfinylamino and ethoxysulfinylamino;

oxysulfonylamino group, preferably methoxysulfonylamino and ethoxysulfonylamino;

optionally substituted alkenyl group, preferably, 1-propenyl, vinyl, nitrovinyl, cyano vinyl, or trifluorovinyl and styryl (optionally substituted with methyl, methoxy, halogen, nitro, trifluoromethane or cyano); and alkynyl group, preferably 1-propynyl, ethynyl or trimethylsilylethynyl.

In a more preferred embodiment of compounds of formulae (I) and (I'), $R_2$ is a substituent group selected from optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl.

In an even more preferred embodiment, $R_2$ is an optionally substituted alkyl, and more preferably a $C_{1-7}$ alkyl group or even more preferably a $C_{1-4}$ alkyl group which has been terminally substituted. Preferred substituents include carboxyl (and derivatives such as esters), optionally substituted amino, optionally substituted heterocyclyl, optionally substituted heteroaryl, and optionally substituted sulfonyl. Preferred optionally substituted amino groups include: $NH_2$, $C_{1-4}$ monoalkylamino, optionally substituted monoarylalkylamino, $C_{1-4}$ dialkylamino, quaternary ammonium salts, optionally substituted benzoyl, optionally substituted sulfonyl, and residues of amino acids and peptides.

Examples of preferred substituent groups for when $R_2$ is a terminally substituted alkyl group include:

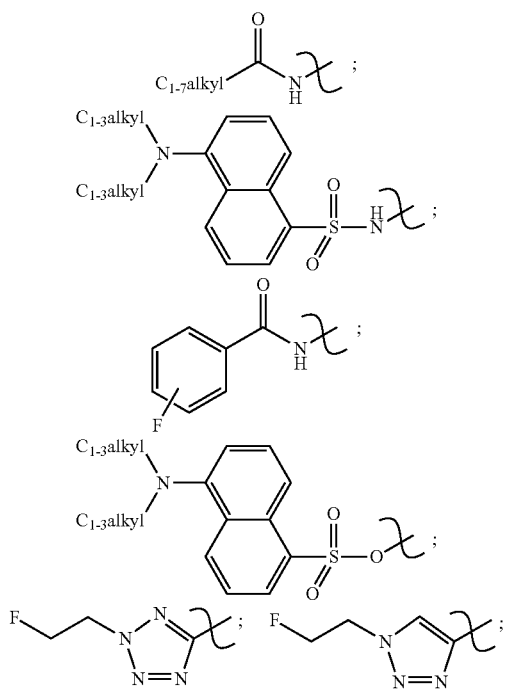

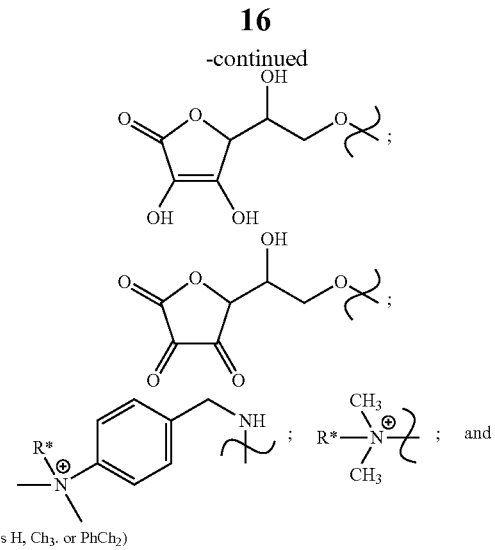

(R* is H, $CH_3$, or $PhCH_2$)

derivatives thereof.

Other preferred substituent groups include residues of amino acids (for example, glycine and glutamic acid), and peptide residues (for example, HIV-tat (YGRKKRRQRRR) and Pentratin (RQIKIWFQNRRMKWKK)).

In an even more preferred embodiment of compounds of formula (I) and (I') as defined above, X is Pt, Pd, or Ru and even more preferably Pt. In this embodiment, n is an integer of 2 or 4.

Thus, in a further embodiment the invention provides a platinum complex of formula (I") or a salt thereof;

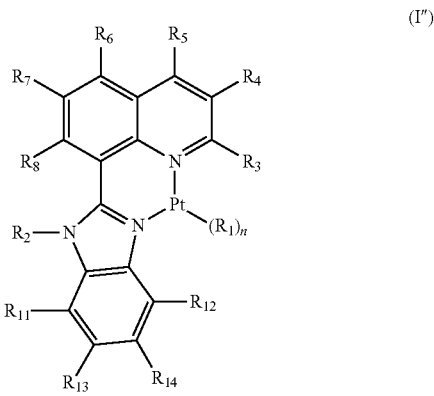

(I")

wherein:
n is an integer of 2 or 4;
each $R_1$ is independently selected from halogen, NR'R''R''' (where each of R', R'', and R''' is independently selected from hydrogen, alkyl, cycloalkyl, aryl, heteroaryl, heterocycyl and oxyacyl), optionally substituted acyloxy, optionally substituted alkoxy, SR'R'' (where each of R' and R'' is independently selected from hydrogen, alkyl, cycloalkyl, aryl, heteroaryl, heterocycyl and oxyacyl), optionally substituted heteroaryl, optionally substituted carbohydrate, or any two $R_1$ form a malonate, oxalate or glycolate;
$R_2$ is selected from optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and wherein each $R_3$-$R_8$ and $R_{11}$-$R_{14}$ independently represents H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy.

In an even more preferred embodiment of compounds of formula (I") $R_2$ is an optionally substituted alkyl, and more preferably a $C_{1-7}$ alkyl group or even more preferably a $C_{1-4}$ alkyl group which has been terminally substituted. Preferred substituents include carboxyl (and derivatives such as esters), optionally substituted amino, optionally substituted heterocyclyl, optionally substituted heteroaryl, and optionally substituted sulfonyl. Preferred optionally substituted amino groups include: $NH_2$, $C_{1-4}$ monoalkylamino, optionally substituted monoarylalkylamino, $C_{1-4}$ dialkylamino, quaternary ammonium salts, optionally substituted benzoyl, optionally substituted sulfonyl, and residues of amino acids and peptides.

Examples of preferred substituent groups for when $R_2$ is a terminally substituted alkyl group include:

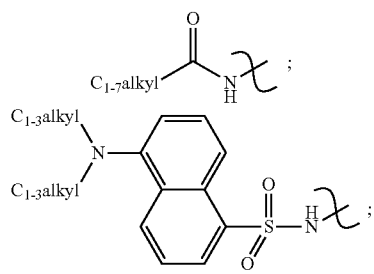

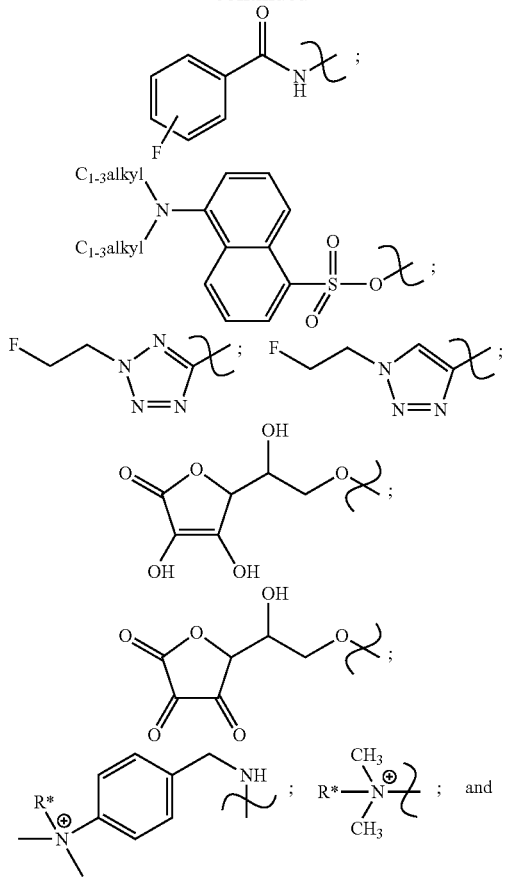

($R^*$ is H, $CH_3$, or $PhCH_2$)

derivatives thereof.

Other preferred substituent groups include residues of amino acids (for example, glycine and glutamic acid), and peptide residues (for example, HIV-tat (YGRKKRRQRRR) and Pentratin (RQIKIWFQNRRMKWKK)).

In relation to the transition metal complexes of formulae (I), (I') and (I") it will be appreciated that the integer n will depend on the valency of the central atom X and the number and also the charge of the ligands $R_1$ present. For instance, where $R_1$ represents a neutral ligand, and with respect to the first series of d-block transition elements, the following preferred oxidation states are contemplated: Mn(II) (4 coordinate, i.e., n=2), Mn(III) (6 coordinate, i.e., n=4), Fe(II) (4 coordinate, i.e., n=2), Fe(III) (6 coordinate, i.e., n=4), Co(II) (4 coordinate, i.e., n=2), Co(III) (6 coordinate, i.e., n=4) and Ni(II) (4 coordinate, i.e., n=2).

It will be appreciated that for compounds of formula (I") as the coordinating ligand is bivalent all of the Pt(II) compounds (4-coordinate, i.e., where n=2) are in the cis-conformation. Pt(IV) compounds are 6-coordinate (i.e., where n=4).

In a preferred embodiment the metal complexes are square planar systems, and preferably Pd, Pt and Ru square planar complexes.

In relation to Pt complexes of formula (I") and wishing to be bound by theory, the Pt(IV) 6-coordinate octahedral systems are also preferred (i.e., n=4) as it is believed that such systems can behave as pro-drugs, providing the active Pt(II) species within the body (in vivo).

In a further embodiment of transition metal complexes of formula (I), (I') and (I"), $R_1$ is halogen, ammonia, optionally substituted acyloxy, optionally substituted oxyacyl, or any two $R_1$ form a malonate, oxalate, or glycolate.

In an embodiment two of $R_1$ form:
(i) a malonate of formula:

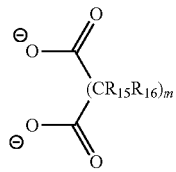

where m is an integer of 1 to 3 and $R_{15}$ and $R_{16}$ are independently selected from hydrogen, optionally substituted alkyl, optionally substituted acylamino, optionally substituted amino, optionally substituted oxyacyl, optionally substituted acyloxy, or $R_{15}$ and $R_{16}$ together form a $C_4$-$C_6$ cycloalkane ring; or
(ii) an oxalate of formula:

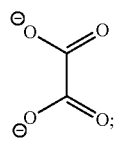

or
(iii) a glycolate of formula:

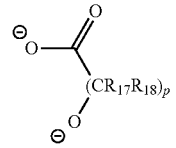

where p is an integer of 1 to 3 and $R_{17}$ and $R_{18}$ are independently selected from hydrogen, optionally substituted alkyl, optionally substituted acylamino, optionally substituted amino, optionally substituted oxyacyl, optionally substituted acyloxy, or $R_{17}$ and $R_{18}$ together form a $C_4$-$C_6$ cycloalkane ring.

Preferably for transition metal complexes of formula (I), (I') and (I") $R_1$ is a halogen, and even more preferably chloro.

In another preferred embodiment n=4 and $R_1$ is a mixture of OH and halogen, preferably chloro. In another preferred embodiment n=4 and $R_1$ is a mixture of optionally substituted acyloxy and halogen, preferably chloro. In an even more preferred embodiment the Pt complex is represented by:

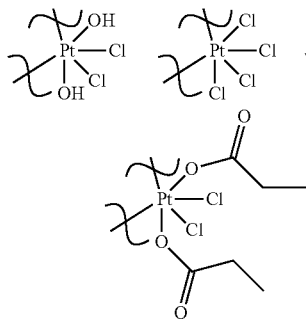

The transitional metal complexes of the present invention are produced by complexing the bidendate ligands of formula (II) with a stabilised reagent transition metal complex.

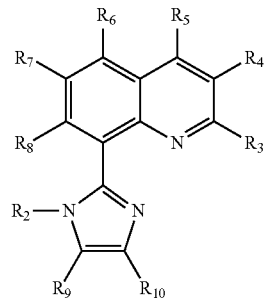

This is preferably achieved by an exchange reaction between the ligand of formula (II) and a stabilising complex of the transitional metal wherein the bond between the metal and stabilising complex is more labile than the bond that is formed between the transitional metal and ligand of formula (II). Generally, the stabilised metal complex will be dissolved in a suitable solvent followed by the addition of the ligand of formula (II). The addition of the ligand can be done either directly as a solid or as a solution in a suitable solvent which may or may not be the same solvent used to dissolve the transition metal complex. In the case where the solvents differ, the solvents are matched so as to avoid precipitation of the reactants from the reaction solvent mixture. Preferred solvents include polar solvents like alcohols, dimethylformamide, or chlorinated solvents like dichloromethane, chloroform, and carbontetrachloride, or aromatic hydrocarbons like benzene and toluene, or ethers like diethylether and tertrahydrofuran. The formation of the transition metal complex can usually be followed by observing colour changes in the reaction mixture or through spectroscopic means, such as for instance, $^{195}$Pt-NMR and/or G.C. The transition metal complexes of the present invention can be recovered by simply removing the reaction solvent in vacuo. The complex may be subjected to further purification according to known techniques or used without additional purification.

As a non-limiting example, the transitional metal complexes of the present invention can be prepared according to scheme 1 below:

Scheme 1

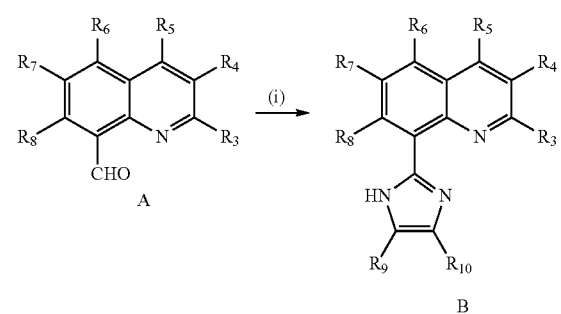

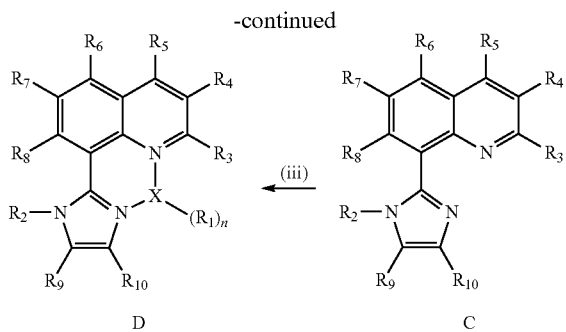

D            C

According to general Scheme 1 the compounds of the present invention as represented by formula D may be prepared by coupling an appropriately substituted aldehyde A with an appropriately substituted imidazole (for example, an optionally substituted benzimidazole) to form B. The coupling reaction may be carried out, for example, by contacting A and the imidazole in 1:1THF/water and heating the resultant mixture under reflux for several hours to 24 hours. The formed coupled product B may be isolated and purified (if required) using standard techniques such as column chromatography.

According to Scheme 1 the $R_2$ group may then be added (see step (ii)) to form a compound of formula C. Where, for instance, $R_2$ is a terminally substituted alkyl moiety step (ii) may be an alkylation reaction involving reacting B with a terminally substituted 1-halo alkyl (e.g. $(CH_3)_2NCH_2CH_2Br$) in a polar solvent in the presence of a suitable base.

Step (iii) in Scheme 1 refers to the metal complexation step to form compounds of formula D. This may occur under standard conditions known in the art, for example, see Fanizzi et al, Inorg. Chem., 1996, 35, 3173, and Braddock and Meyer, JACS., 1973, 95, 3158.

The complexes of the present invention where X is Pt may be formed by reacting Pt stabilised complexes such as [Pt(DMSO)$_2$Cl$_2$] with formula C. Other suitable metal stabilising complexes for Pd, Tc, Mn, Fe, Co, Ni, Ru, Au, Re, Rh, Hg are known in the literature or are commercially available, such as for example, hexachloride salts of Mn or trichloride or tetrachloride salts of Ru (e.g. RuCl$_3$ and RuCl$_4$).

During the reactions described above a number of the moieties may need to be protected. Suitable protecting groups are well known in industry and have been described in many references such as Protecting Groups in Organic Synthesis, Greene T W, Wiley-Interscience, New York, 1981.

Other compounds of formulae (I), (I') and (I'') can be prepared by the addition, removal or modification of existing substituents. This could be achieved by using standard techniques for functional group inter-conversion that are well known in the industry, such as those described in "Comprehensive organic transformations: a guide to functional group preparations" by Larock R. C., New York, VCH Publishers, Inc. 1989.

Examples of functional group inter-conversions are: —C(O)NR*R** from —CO$_2$CH$_3$ by heating with or without catalytic metal cyanide, e.g. NaCN, and HNR*R** in CH$_3$OH; —OC(O)R from —OH with e.g., ClC(O)R in pyridine; —NC(S)NR*R** from —NHR with an alkylisothiocyanate or thiocyanic acid; —NRC(O)OR* from —NHR with alkyl chloroformate; —NRC(O)NR*R** from —NHR by treatment with an isocyanate, e.g. HN=C=O or RN=C=O; —NRC(O)R* from —NHR by treatment with ClC(O)R* in pyridine; —C(=NR)NR*R** from —C(NR*R**)SR with H$_3$NR$^+$OAc$^-$ by heating in alcohol; —C(NR*R**)SR from —C(S)NR*R** with R—I in an inert solvent, e.g. acetone; —C(S)NR*R** (where R* or R** is not hydrogen) from —C(S)NH$_2$ with HNR*R**; —C(=NCN)—NR*R** from —C(=NR*R**)—SR with NH$_2$CN by heating in anhydrous alcohol, alternatively from —C(=NH)—NR*R** by treatment with BrCN and NaOEt in EtOH; —NR—C(=NCN)SR from —NHR* by treatment with (RS)$_2$C=NCN; —NR**SO$_2$R from —NHR* by treatment with ClSO$_2$R by heating in pyridine; —NR*C(S)R from —NR*C(O)R by treatment with Lawesson's reagent [2,4-bis(4-methoxyphenyl)-1,3,2,4-dithiadiphosphetane-2,4-disulfide]; —NRSO$_2$CF$_3$ from —NHR with triflic anhydride and base, —CH(NH$_2$)CHO from —CH(NH$_2$)C(O)OR* with Na(Hg) and HCl/EtOH; —CH$_2$C(O)OH from —C(O)OH by treatment with SOCl$_2$ then CH$_2$N$_2$ then H$_2$O/Ag$_2$O; —C(O)OH from —CH$_2$C(O)OCH$_3$ by treatment with PhMgX/HX then acetic anhydride then CrO$_3$; R—OC(O)R* from RC(O)R* by R**CO$_3$H; —CCH$_2$OH from —C(O)OR* with Na/R*OH; —CHCH$_2$ from —CH$_2$CH$_2$OH by the Chugaev reaction; —NH$_2$ from —C(O)OH by the Curtius reaction; —NH$_2$ from —C(O)NHOH with TsCl/base then H$_2$O; —CHC(O)CHR from —CHCHOHCHR by using the Dess-Martin Periodinane regent or CrO$_3$/aqH$_2$SO$_4$/acetone; —C$_6$H$_5$CHO from —C$_6$H$_5$CH$_3$ with CrO$_2$Cl$_2$; —CHO from —CN with SnCl$_2$/HCl; —CN from —C(O)NHR with PCl$_5$; —CH$_2$R from —C(O)R with N$_2$H$_4$/KOH.

From the above schemes it can be observed that compounds of formula (II) are key intermediates in the preparation of the transition metal complexes of the present invention.

Accordingly, in another aspect the invention provides novel compound of formula (II) or a salt thereof:

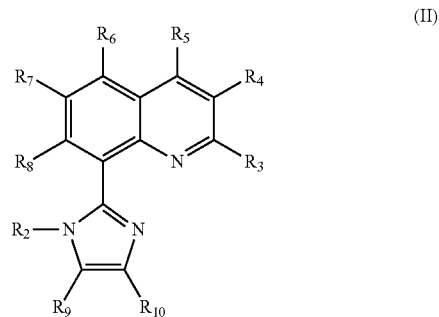

(II)

wherein
$R_2$ is selected from optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and
wherein each of $R_3$-$R_{10}$ independently represents H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihaloethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or $R_9$ and $R_{10}$ together form an optionally substituted aryl, optionally substituted heteroaryl, or optionally substituted cycloalkenyl.

Preferably, the compounds of formula (II) are compounds or salts of formula (II'):

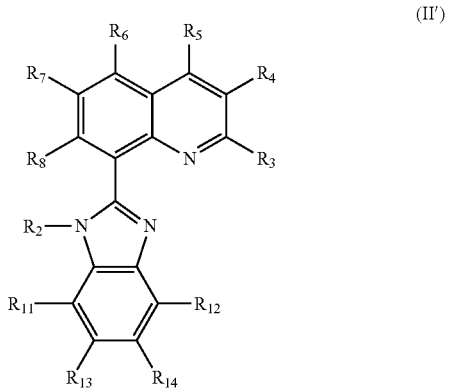

(II')

wherein
  $R_2$ is selected from optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and
  wherein each of $R_3$-$R_8$ and $R_{11}$-$R_{14}$ independently represents H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy.

Preferably, for compounds of formula (II') $R_2$ is an optionally substituted alkyl and more preferably a $C_{1-7}$ alkyl group (even more preferably $C_{1-4}$ alkyl group) terminally substituted.

Without wishing to be bound by theory it is believed that the transition metal complexes of the present invention act by binding to amyloid proteins which form neuritic plaques.

The blood-brain barrier (BBB) is a membrane structure composed of endothelial cells which are packed tightly within brain capillaries. The BBB acts to protect the brain from common infections and the many chemicals flowing within the blood, whilst allowing essential metabolic brain function. Only smaller molecules of a certain chemical nature and with a molecular weight lower than 500 daltons (500 u) may traverse the BBB and this presents significant difficulty in the delivery of therapeutic agents to specific regions of the brain. Many drug candidate molecules that might otherwise be effective in diagnosis and therapy in cell culture do not cross the BBB in adequate amounts, rendering them ineffective in the treatment of patients suffering from a brain disease. Another advantages of the present invention is that the preferred compounds of the present invention are designed to traverse the BBB.

Thus, the compounds of the present invention may be used in treating a variety of amyloid forming disorders. Such disorders include diabetes mellitus type 2, Alzheimer's disease (AD), Parkinson's disease, Huntington's disease, Creutzfeldt-Jakob disease, congestive heart failure, bovine spongiform encephalopathy and age related Macular Degeneration (AMD).

The invention also provides for the use of a compound of formulae (I), (I'), or (I'') in the manufacture of a medicament for treating an amyloid disorder.

There is also provided a method of treating an amyloid disorder comprising the administration of an effective amount of at least one transition metal complex of formula (I), (I'), or (I''), to a subject in need thereof.

The transition metal complexes of the invention may be particularly useful in combination therapy. In a combination therapy it is intended to include any chemically compatible combination of pharmaceutically-active agents, as long as the combination does not eliminate the activity of the complexes of formula (I), (I') or (I''). It will be appreciated that the complexes of the invention and the other medicaments may be administered separately, sequentially or simultaneously.

Where the condition is amyloidosis, other medicaments may include: diuretics to control fluid retention; melphalan (Alkeran—an agent also used to treat some cancers); corticosteroids for anti-inflammation; anti-arrhythmics to control heart rhythm or; antibiotics to control bacteria that may cause diarrhea or prevent the body from absorbing nutrients. Further agents may include statins, estrogen, ginkgo biloba, antidepressants, antipsychotics or mood stabilizers.

Where the amyloidosis condition is a β-amyloid related condition, particularly Alzheimer's disease, other medicaments may include: Cholinesterase inhibitors (ChEIs) such as donepezil, rivastigmine, and galantamine; an antioxidant, such as Vitamin E or Vitamin C; an anti-inflammatory agent such as flurobiprofen or ibuprofen optionally modified to release nitric oxide (for example NCX-2216, produced by NicOx); the N-methyl-D-aspartate (NMDA) antagonist, memantine; or an oestrogenic agent such as 17-β-oestradiol.

For therapeutic applications, the compounds of the invention are administered to the subject in a treatment effective amount. As used herein, a treatment effective amount is intended to include at least partially attaining the desired effect, or delaying the onset of, or inhibiting the progression of, or halting or reversing altogether the onset or progression of the particular amyloid disease of condition being treated.

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage may be in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another preferred embodiment, the dosage may be in the range of 1 mg to 100 mg per kg of body weight per dosage, such as up to 50 mg per body weight per dosage.

Suitable dosage amounts and dosing regimens can be determined by the attending physician and may depend on the particular condition being treated, the severity of the condition as well as the general age, health and weight of the subject.

The term "subject" or "patient" as used herein refers to any animal having a disease or condition which requires treatment or prophylaxis with a pharmaceutically-active agent.

The subject or patient may be a mammal, preferably a human, or may be a non-human primate or non-primates such as used in animal model testing. While it is particularly contemplated that the complexes of the invention are suitable for use in the medical treatment of humans, they may also be applicable to veterinary treatment, including treatment of companion animals such as dogs and cats, and domestic animals such as horses, ponies, donkeys, mules, llama, alpaca, pigs, cattle and sheep, or zoo animals such as primates, felids, canids, bovids and ungulates.

The transition metal complexes of the present invention may be administered in a single dose or a series of doses. While it is possible for the active ingredient to be administered alone, it is preferable to present it as a composition, preferably as a pharmaceutical or veterinary composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically or veterinary "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste. With specific focus on veterinary use the oral compositions may be in the form of drenches; powders, granules or pellets for admixture with feed stuffs; or pastes for application to the tongue.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described. With specific focus on veterinary compositions parenteral administration includes intramammary injection where a suspension or solution is introduced in the udder via the teat.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Preferably, the transition metal complexes of the present invention may be administered to a subject as a pharmaceutically acceptable salt. It will be appreciated however that non-pharmaceutically acceptable salts also fall within the scope of the present invention since these may be useful as intermediates in the preparation of pharmaceutically acceptable salts or in veterinary applications. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts eg sodium or potassium salts, or alkyl esters (eg methyl, ethyl) of the phosphate group.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will be appreciated that any compound that is a prodrug of a transition metal complexes of formula (I), (I'), or (I'') is also within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group (for instance at the $R^2$ position) is converted into an ester, such as an acetate or phosphate ester, or where a free amino group is (for instance at the $R^2$ position) converted into an amide (eg. α-aminoacid amide). Procedures for esterifying, eg. acylating, the compounds of the invention are well known in the art and may include treatment of the compound with an appropriate carboxylic acid, anhydride or chloride in the presence of a suitable catalyst or base.

The complexes of the invention may be in crystalline form either as the free compounds or as solvates (e.g. hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, eg., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

Apart from therapeutic uses, the metal complexes of the present invention may be useful as diagnostic tools. In a further aspect the invention provides transition metal complexes of formula (I), (I'), and (I'') which are suitably substituted with $^{131}$I, $^{123}$I, $^{76}$Br, $^{75}$Br, $^{18}$F, $^{19}$F, or a fluorescent moiety. Such complexes may be useful in amyloid imaging techniques for diagnosing amyloid diseases in vivo (i.e., ante-mortem). Such complexes which can be viewed as "labelled" probes may also be useful in quantitation of amyloid deposits in biopsy or post-mortem tissue specimens.

In a further embodiment the invention provides a method of diagnosing an amyloid disorder comprising:
  (i) administering a detectable quantity of a transition metal complex of formula (I), (I'), or (I'') or a salt thereof to a patient, and
  (ii) detecting the binding of the transition metal complex to an amyloid deposit in said patient, wherein the transition metal complex or salt thereof is characterised with at least one label consisting of $^{131}$I, $^{123}$I, $^{76}$Br, $^{75}$Br, $^{8}$F, $^{19}$F, or a fluorescent moiety.

The method described above may be used to diagnose a patient who is suspected of having an amyloidosis associated disease. The method can also be used to determine the presence, size and location of amyloid deposits in the body (preferably the brain) of the patient.

The diagnostic methods disclosed herein refer to the use of labelled transition metal complexes of the present invention in conjunction with non-invasive imaging techniques such as magnetic resonance spectroscopy (MRS), magnetic resonance imaging (MRI), gamma imaging such as position emission tomography (PET) or single-photon emission computed tomography (SPECT). Such techniques can be used to quantify and diagnose amyloid depositions in vivo. For the purposes of in vivo imaging, the type of instrumentation used for diagnosis is dependant on the specific label. For example, radioactive isotopes and $^{19}$F are suitable for the diagnostic methods described herein. When choosing a suitable label the factors to consider include type of decay which is to be detected and half-life of the chosen radionuclide. Suitable radioisotopes include beta-emmiters, gamma-emitters, positron-emitters, and x-ray emitters including $^{131}$I, $^{123}$I, $^{18}$F, $^{75}$Br and $^{76}$Br. Suitable stable isotopes for use in MRI or MRS include $^{19}$F. Suitable radioisotopes for biopsy or analysis of post-mortem tissue include $^{125}$I. Preferred radiolabels are $^{18}$F for PET analysis, $^{123}$I for SPECT imaging and $^{19}$F for MRS/MRI.

The radiolabels may be added to an existing compound of formula (I), (I'), or (I") using standard chemistry or incorporated during the synthesis of compounds of formula (I), (I'), or (I").

Preferably the radiolabel is added to or forms part of the $R_2$ group in compounds of formula (I), (I'), or (I").

Likewise to assist in determining how readily the compounds of the invention permeate the blood-brain barrier, $R_2$ may advantageously comprise a chromophore, a fluorophore or a chemiluminescent label, collectively referred to herein as a "fluorescent moiety". In one embodiment, $R_2$ comprises a chromophore. Suitable chromophores would be known by a person skilled in the art and include a wide range of aryl and heteroaryl compounds. Such chromophores may advantageously be detected following irradiation with ultra-violet light. In one embodiment, the chromophore is a naphthyl derivative, a 1,2,3-triazole derivative or a tetrazole derivative. In another embodiment, $R_2$ is selected from any one of the following substituents:

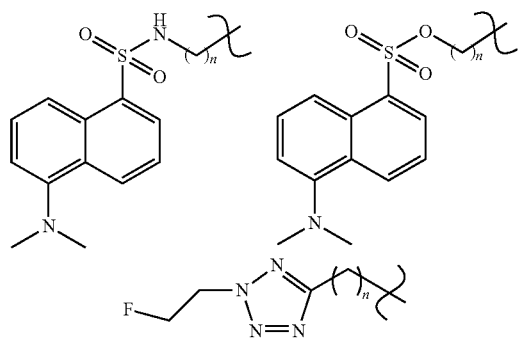

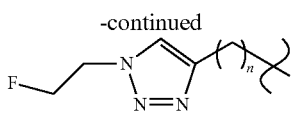

where n=1-7

In other embodiments, $R_2$ comprises a fluorescent or a chemiluminescent label. Suitable labels would be known by a person skilled in the art. For example, fluorescent labelling compounds include: fluorescein, fluorescein isothiocyanate, rhodamine, methylrhodamine, tetramethylrhodamine, phycoerythrin, phycocyanin, allophycocyanin, o-phthaldehyde, auramine, Texas Red, AMCA blue, Lucifer Yellow, fluorescamine and derivatives thereof. Chemiluminescent labelling compounds, for example, include: luminol, isoluminol, theromatic acridium ester, imidazole, acridinium salt, oxalte ester, luciferin and derivatives thereof.

The amount of administered labelled transition metal complex to be used in the diagnosis method will depend on the age, sex, weight and condition of the patient. This can be adjusted as required by a skilled physician. It will be appreciated by those in the art that the quantity of the labelled probe required for diagnostic imaging will be relatively minute. Dosages can range from 0.001 mg/kg to 1000 mg/kg, however smaller quantities in the range of 0.1 mg/kg to 100 mg/kg will be preferred.

The attending diagnostic physician may administer the labelled transition metal complex of the present invention either locally or systemically (for instance, intravenously, intrathecally, intraarterially, and so on). After administration the labelled transition metal complex is allowed sufficient time to bind with an amyloid protein. This can take between 30 minutes to 2 days. The area of the patient under investigation is then scanned by the standard imaging techniques discussed above. In relation to brain imaging, for example AD diagnosis, preferably the amount of the bound labelled transition metal complex (total and specific binding) is measured and compared as a ratio with the amount of labelled transition metal complex bound to the cerebellum of the patient. This ratio is then compared to the same ratio in an age-matched normal brain.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

Certain embodiments of the invention will now be described with reference to the following examples which are intended for the purpose of illustration only and are not intended to limit the scope of the generality hereinbefore described.

EXAMPLES

Synthetic Protocols

A—Synthesis of Ligands of Formula (C)

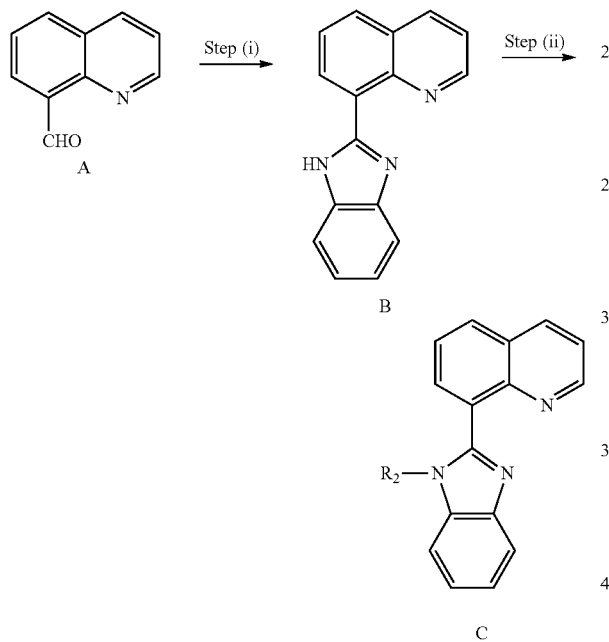

Step (i)—General Procedure (I)—Benzimidazoles:

A solution of aldehyde A (10 mmol) and a o-phenylenediamine (10 mmol) in 1:1 THF/Water (30 ml) was stirred at refluxing temperature for 24 h. The reaction mixture was cooled and diluted with ethyl acetate (100 ml). The organic layer was separated and washed with brine and dried over anhydrous sodium sulfate. The solution was concentrated in vacuo and subjected to column chromatography (silica gel, ethylacetate and petroleum ether) to give the benzimidazole B.

Step (ii)—General Procedure (II)—Alkylation of Benzimidazoles:

A solution of benzimidazole B (10 mmol), o-substituted alkyl chloride hydrochloride (12 mmol) and cesium carbonate (30 mmol) in DMF (30 ml) was stirred at 80° C. for overnight. The reaction mixture was cooled, poured into ice-water and extracted with dichloromethane. The organic layer was washed with water, brine and dried over anhydrous sodium sulfate. The solution was concentrated in vacuo and subjected to column chromatography (silica gel) to give the product C.

B—Synthesis of Complexes of Formula (D)

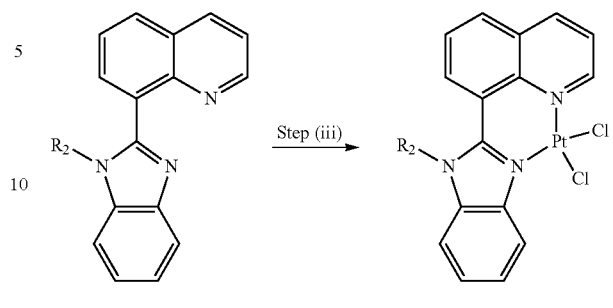

Step (iii)—General Procedure (III)—Platinum (II) Complex Formation:

A solution of free ligand C (1 mmol) in methanol (10 ml) was added [Pt(DMSO)$_2$Cl$_2$] (1 mmol) and stirred at room temperature for 48-60 h. A solid of platinum (II) complex precipitated which was isolated by filtration. Complex D may be analysed by $^1$H NMR, $^{195}$Pt NMR and mass spectrometry.

C—Synthesis of Complexes of Formula (E)

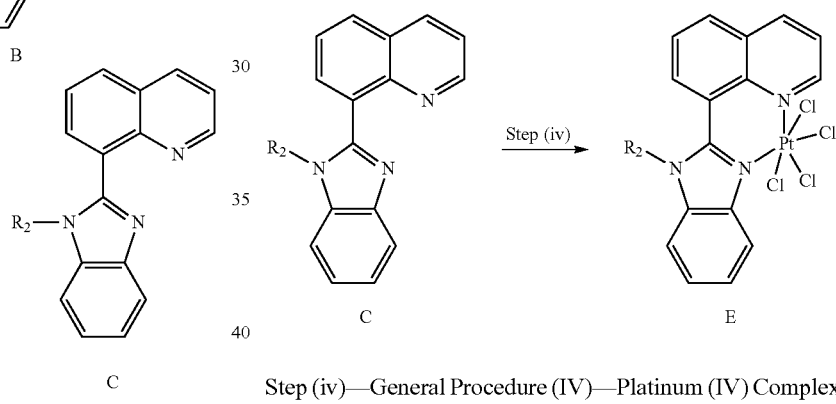

Step (iv)—General Procedure (IV)—Platinum (IV) Complex Formation:

A stoichiometric amount of free ligand C and hexachloroplatinic acid {H$_2$[PtCl$_6$].6H$_2$O} was added in dimethyl sulfoxide at room temperature for 4-5 days. The reaction mixture was poured in dilute aqueous sodium bicarbonate to give a precipitate. The solid was isolated by filtration and washed with methanol followed by ether to give the platinum (IV) complex E. The complex may be analysed by $^1$H NMR, $^{195}$Pt NMR and mass spectrometry.

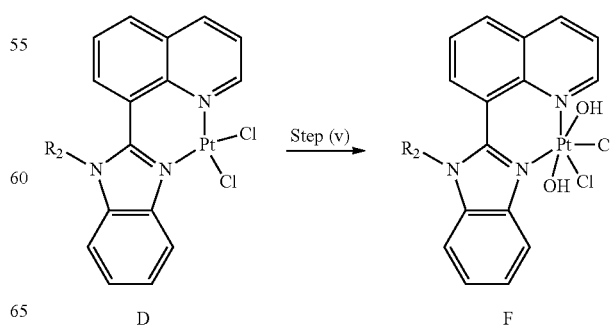

Step (v)—General Procedure (V)—Alternate Platinum (IV) Complex Formation

D (1 mmol) was suspended in acetone (6 mL) to which was added H₂O₂ (35 wt % aq, 6 mL). The reaction mixture was stirred at 50° C. for 16 h. The homogeneous mixture was cooled and concentrated in vacuo. The residue was diluted with water (20 mL) to give a solid which was isolated by filtration to yield F.

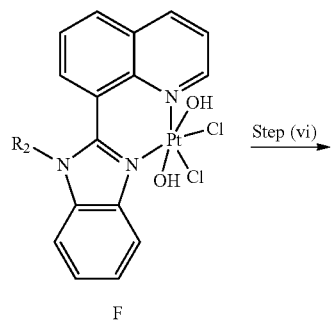

F

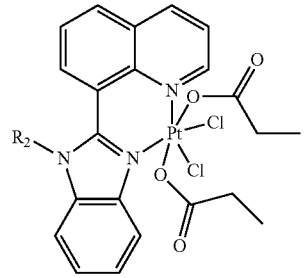

G

Step (vi)—A General Procedure (VI)—a Further Alternative to Platinum (IV) Complex Formation The oxidized product F (200 mg) was taken in dichloromethane (10 mL) to which was added propionic anhydride (0.5 mL). The mixture was stirred at refluxing temperature for 24 h. A solution was obtained, which was then evaporated under reduced pressure. The oily residue was suspended in water and stirred at room temperature for 2 h. The solution was extracted with dichloromethane and the organic layer was washed with water, brine and dried over Na₂SO₄. The solution was concentrated in vacuo and the residue was subjected to column chromatography (silica gel, acetone-dichloromethane) to give the required product G is reasonable yield (optimization in progress).

Example 1

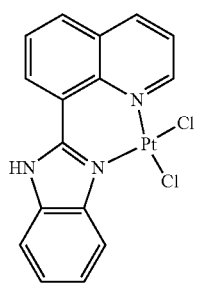

Prepared by Following General Procedures I and III.
$^1$H NMR (DMSO): δ 13.41 (br s, 1H), 9.57 (d, J=4.8 Hz, 1H), 8.85 (d, J=8 Hz, 1H), 8.71 (d, J=7.2 Hz, 1H), 8.42 (d, J=8.4 Hz, 1H), 8.32 (d, J=8 Hz, 1H), 8.0 (dd, J=8, 7.6 Hz, 1H), 7.68 (dd, J=8.4, 5.2 Hz, 1H), 7.62 (d, J=7.6 Hz, 1H), 7.37 (m, 2H);
ESI-MS (CH₃CN—H₂O, -ve mode): m/z 510 [M–H]⁻.

Example 2

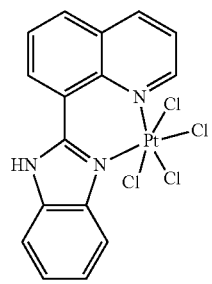

Prepared by following general procedures I and IV.
$^1$H NMR (DMSO, 500 MHz): δ 14.82 (br s, 1H), 9.77 (dd, $J_{H-H}$=5.5 Hz, $J_{H-Pt}$=30 Hz, 1H), 9.05 (d, J=8 Hz, 1H), 8.80 (d, J=7.5 Hz, 1H), 8.64 (m, 1H), 8.53 (d, J=8.5 Hz, 1H), 8.12 (dd, J=8, 7.5 Hz, 1H), 8.0 (d, J=8 Hz, 1H), 7.76 (m, 1H), 7.4 (m, 2H);
ESI-MS (CH₃CN—H₂O, -ve mode): m/z 581[M–H]⁻.

Example 3

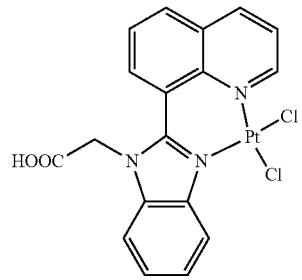

Prepared by following general procedures I, II and III.
$^1$H NMR (DMSO, 500 MHz): δ 9.47 (d, J=5.2 Hz, 1H), 8.86 (d, J=7 Hz, 1H), 8.54 (d, J=7 Hz, 1H), 8.48 (m, 1H), 8.44 (d, J=7.5 Hz, 1H), 7.99 (dd, J=8, 7.5 Hz, 1H), 7.8 (m, 1H), 7.70 (dd, J=8.5, 8.5 Hz, 1H), 7.45 (m, 2H), 5.2 (br s, 2H);
$^{195}$Pt NMR* (DMSO): δ –2011.

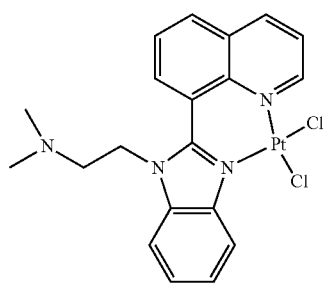

Example 4

Prepared by following general procedures I, II and III, and recovered as a yellow solid.

$^1$H NMR (DMSO): δ 9.47 (dd, J=4.4, 1.2 Hz, 1H), 8.87 (m, 2H), 8.50 (dd, J=6.8, 2.4 Hz, 1H), 8.46 (d, J=8 Hz, 1H), 8.03 (dd, J=8, 7.6 Hz, 1H), 7.84 (m, 1H), 7.68 (dd, J=8.4, 5.2 Hz, 1H), 7.45 (m, 2H), 4.42 (br t, 2H), 1.75 (br t, 2H), 1.87 (s, 3H);

$^{195}$Pt NMR* (DMSO): δ −2001.

Example 5

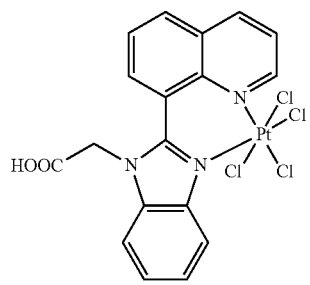

Prepared by following general procedures I, II and IV.

$^1$H NMR (DMSO): δ 9.67 (dd, $J_{H-H}$=5.6 Hz, $J_{H-Pt}$=33.2 Hz, 1H), 9.05 (d, J=8 Hz, 1H), 8.86 (m 1H), 8.53 (d, J=8 Hz, 1H), 8.45 (d, J=7.2 Hz, 1H), 8.0 (m, 2H), 7.90 (m, 1H), 7.56 (m, 2H), 5.33 (br s, 2H);

$^{195}$Pt NMR* (DMSO): δ −2.11;

ESI-MS (CH$_3$CN—H$_2$O, −ve mode): m/z 638 [M-H]$^-$.

Example 6

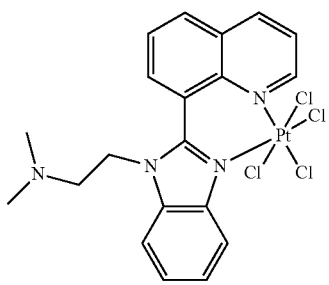

Prepared by following general procedures I, II and IV.

$^1$H NMR (DMSO): δ 9.63 (dd, $J_{H-H}$=5.6 Hz, $J_{H-Pt}$=33.2 Hz, 1H), 9.05 (d, J=8 Hz, 1H), 8.96 (m 1H), 8.83 (m, 1H), 8.53 (d, J=8 Hz, 1H), 8.09 (m, 2H), 7.94 (m, 1H), 7.55 (m, 2H), 4.48 (br m, 2H), 2.69 (br m, 2H), 1.92 (br s, 3H);

$^{195}$Pt NMR* (DMSO): δ −2.11;

ESI-MS (CH$_3$CN—H$_2$O, −ve mode): m/z 689 [M+K]$^-$ 582 [M−2×Cl].

Example 7

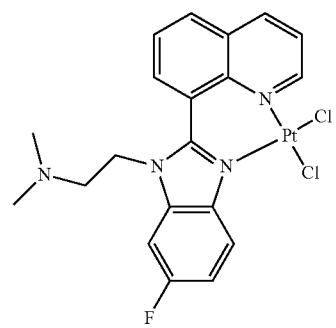

Prepared by following general procedures I, II, and III.

$^1$H NMR (DMSO): δ 9.44 (d, J=4.8 Hz, 1H), 8.87 (dd, J=8, 7.2 Hz, 2H), 8.50 (dd, J=9.2, 5.2 Hz, 1H), 8.46 (d, J=8.4 Hz, 1H), 8.02 (dd, J=8, 7.6 Hz, 1H), 7.84 (dd, J=9.2, 2.4 Hz, 1H), 7.68 (dd, J=8.4, 5.2 Hz, 1H), 7.37 (m, 1H), 4.40 (br t, 2H), 2.46 (br t, 2H), 1.81 (s, 3H).

Example 8

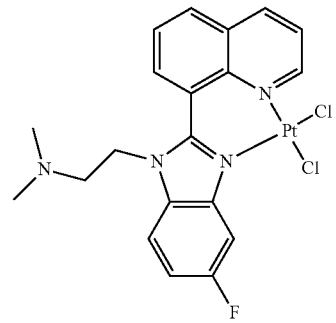

Prepared by following general procedures I, II and III.

$^1$H NMR (DMSO): δ 9.46 (d, J=4.8 Hz, 1H), 8.87 (dd, J=8, 7.2 Hz, 2H), 8.4 (d, J=8 Hz, 1H), 8.24 (dd, J=9.6, 2.8 Hz, 1H), 8.03 (dd, J=8, 7.6 Hz, 1H), 7.92 (dd, J=9.2, 4.8 Hz, 1H), 7.70 (dd, J=8, 5.6 Hz, 1H), 7.34 (m, 1H), 4.42 (br t, 2H), 2.50 (br t, 2H), 1.84 (s, 3H).

Example 9

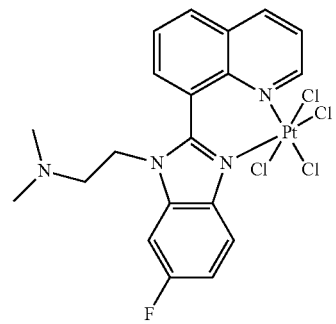

Prepared by following general procedures I, II and IV.
$^1$H NMR (DMSO): δ 9.63 (dd, $J_{H-H}$=5.6 Hz, $J_{H-Pt}$=33.2 Hz, 1H), 9.06 (d, J=7.6 Hz, 1H), 8.85 (dd, J=9.2, 4.8 Hz, 1H), 8.56 (d, J=8.4 Hz, 1H), 8.09 (m, 4H), 7.51 (m, 1H), 4.57 (br m, 2H), 3.87 (br m, 2H), 2.87 (br s, 3H).

Example 10

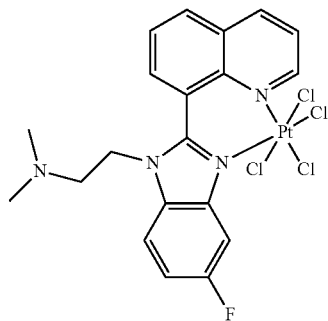

Prepared by following general procedures I, II and IV.
$^1$H NMR (DMSO): δ 9.63 (dd, $J_{H-H}$=5.6 Hz, $J_{H-Pt}$=33.6 Hz, 1H), 9.06 (d, J=8 Hz, 1H), 8.60 (m, 3H), 8.10 (m, 3H), 7.60 (m, 1H), 4.67 (br m, 2H), 3.86 (br m, 2H), 2.92 (br s, 3H).

Example 11

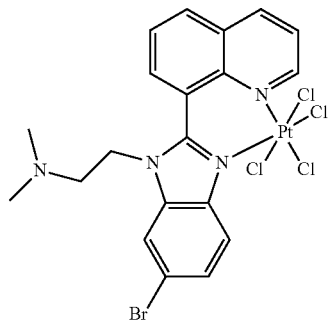

Prepared by following general procedures I, II and IV.
$^1$H NMR (DMSO): δ 9.63 (dd, $J_{H-H}$=5.2 Hz, $J_{H-Pt}$=32.8 Hz, 1H), 9.06 (d, J=7.2 Hz, 1H), 8.76 (d, J=8.8 Hz, 1H), 8.56 (d, J=8 Hz, 1H), 8.35 (br s, 1H), 8.11 (m, 2H), 8.07 (dd, J=8, 5.6 Hz, 1H), 7.76 (d, J=8.8 Hz, 1H), 4.6 (br m, 2H), 2.87 (br m, 2H), 1.97 (br s, 3H);
$^{195}$Pt NMR* (DMSO): δ 25.63.

Example 12

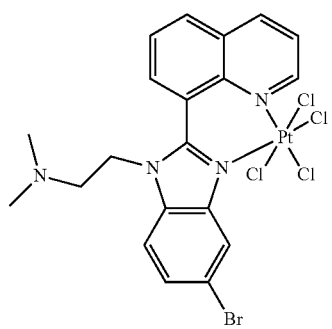

Prepared by following general procedures I, II and IV.
$^1$H NMR (DMSO): δ 9.63 (dd, $J_{H-H}$=5.2 Hz, $J_{H-Pt}$=32.4 Hz, 1H), 9.07 (d, J=7.2 Hz, 1H), 9.04 (d, J=2 Hz, 1H), 8.57 (d, J=8 Hz, 1H), 8.12 (m, 2H), 8.07 (dd, J=8, 6.8 Hz, 1H), 8.07 (dd, J=8, 5.6 Hz, 1H), 8.01 (m, 2H), 7.79 (br d, J=8.8 Hz, 1H), 4.6 (br m, 2H), 2.87 (br m, 2H), 1.97 (br s, 3H);
$^{195}$Pt NMR* (DMSO): δ 24.46.

Example 13

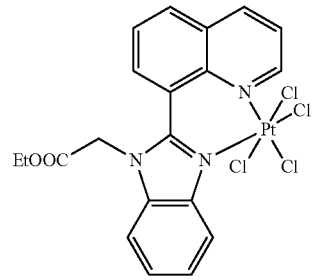

Prepared by esterification of Example 5.
$^1$H NMR (DMSO, 500 MHz): δ 9.66 (dd, $J_{H-H}$=5.5 Hz, $J_{H-Pt}$=32.5 Hz, 1H), 9.07 (dd, J=8, 1.5 Hz, 1H), 8.85 (m, 1H), 8.55 (d, J=7.5 Hz, 1H), 8.47 (d, J=7.5 Hz, 1H), 8.10 (dd, J=8, 5.5 Hz, 1H), 8.07 (t, J=8 Hz, 1H), 7.92 (m, 1H), 7.58 (m, 2H), 5.5 (br s, 2H), 2.87 (q, J=7 Hz, 2H), 1.97 (t, J=7 Hz, 3H);
$^{195}$Pt NMR* (DMSO): δ 32.86;
ESI-MS (CH$_3$CN—H$_2$O, −ve mode): m/z 667.

Example 14

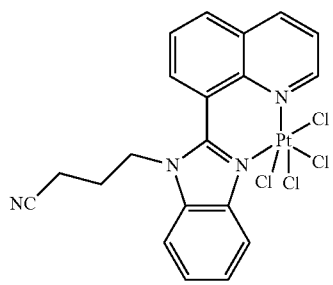

Prepared by following general procedures I, II and IV.
NMR (DMSO): δ 9.65 (dd, $J_{H-H}$=5.5 Hz, $J_{H-Pt}$=32.5 Hz, 1H), 9.05 (d, J=8 Hz, 1H), 8.83 (d, J=8 Hz, 1H), 8.55 (dd, J=6.5, 3 Hz, 2H), 8.08 (dd, J=7.5, 7.5 Hz, 2H), 7.99 (d, J=8 Hz, 1H), 7.57 (m, 2H), 4.35 (br m, 2H), 2.76 (t, J=6.5 Hz, 2H), 2.45 (br m, 2H)

Example 15

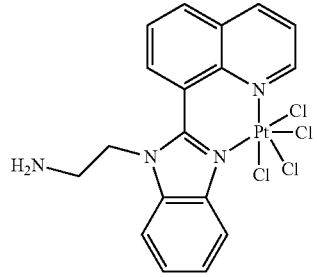

Prepared by following general procedures I, II and N.
$^1$H NMR (DMSO): δ 9.65 (dd, $J_{H-H}$=5 Hz, $J_{Pt}$=23 Hz, 1H), 9.07 (d, J=8.5 Hz, 1H), 8.86 (d, J=7.5 Hz, 1H), 8.56 (d, J=7.5, 1H), 8.52 (d, J=7.5, 1H), 8.08 (m, 2H), 8.02 (d, J=8 Hz, 1H), 7.60 (m, 2H), 4.50 (br m, 2H), 3.57 (br m, 2H)

Example 16

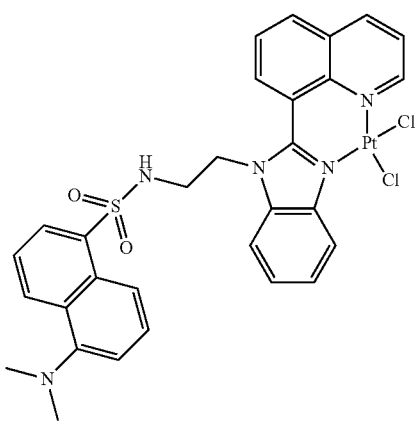

Prepared by following general procedures I, II and IV.

¹H NMR (DMSO): δ 9.46 (dd, J=5.5, 1.5 Hz, 1H), 8.87 (dd, J=8.5, 1.5 Hz, 1H), 8.70 (d, J=7.5 Hz, 1H), 8.47 (m, 1H), 8.45 (d, J=8 Hz, 1H), 8.40 (d, J=8.5 Hz, 1H), 8.12 (t, J=6 Hz, 1H, —NH), 8.0 (d, J=8.5 Hz, 1H), 7.9 (t, J=8 Hz, 1H), 7.80 (d, J=6.5 Hz, 1H), 7.67 (m, 2H), 7.53 (dd, J=8.5, 7.5 Hz, 1H), 7.49 (dd, J=8.5, 8.5 Hz, 1H), 7.44 (m, 2H), 7.21 (d, J=8 Hz, 1H), 4.41 (br peak, 2H), 3.12 (br peak, 2H), 2.8 (s, 6H)

ESI-MS (CH₃CN—H₂O, −ve mode): m/z 787.9

Example 17

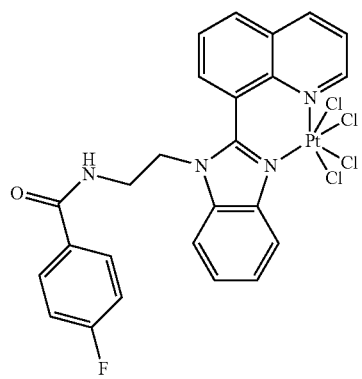

Prepared by following general procedures I, II and IV.

¹H NMR (DMSO): δ 9.55 (dd, $J_{H-H}$=5.5 Hz, $J_{H-Pt}$=32.5 Hz, 1H), 8.86 (d, J=8.5 Hz, 1H), 8.79 (d, J=7, 2H), 8.40 (br t, J=5 Hz, 1H, —NH), 8.35 (d, J=8 Hz, 1H), 8.08 (m, 2H), 7.87 (dd, J=7.5, 6 Hz, 1H), 7.56 (m, 2H), 7.43 (dd, J=8, 8 Hz, 2H), 7.12 (dd, J=9, 8.5 Hz, 2H), 4.72 (br m, 2H), 3.61 (br m, 2H).

Example 18

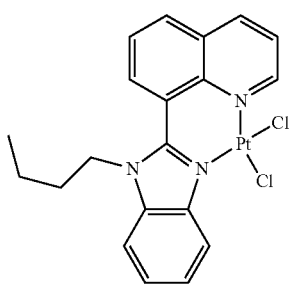

Prepared by following general procedures I, II and III.

¹H NMR (DMSO): δ 9.47 (dd, J=5, 1.5 Hz, 1H), 8.88 (dd, J=8, 1.5 Hz. 1H), 8.61 (d, J=7.5 Hz, 1H), 8.47 (m, 2H), 8.05 (dd, J=8, 7.5 Hz, 1H), 7.84 (m, 1H), 7.69 (dd, J=8.5, 5 Hz, 1H), 7.47 (m, 2H), 4.29 (br peak, 2H), 1.76 (m, 2H), 1.25 (m, 2H), 0.82 (t, J=7.5 Hz, 3H)

Example 19

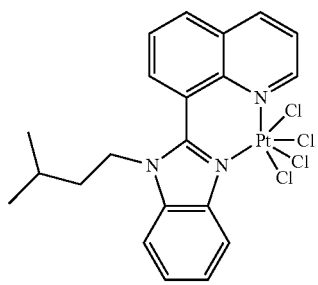

Prepared by following general procedures I, II and IV.

¹H NMR (DMSO): δ 9.63 (dd, $J_{H-H}$=5.5 Hz, $J_{H-Pt}$=36.5 Hz, 1H), 9.06 (d, J=7.5 Hz, 1H), 8.83 (d, J=8.5 Hz, 1H), 8.56 (d, J=7 Hz, 1H), 8.54 (d, J=8 Hz, 1H), 8.13 (dd, J=8, 7.5 Hz, 1H), 8.08 (dd, J=8.5, 5.5 Hz 1H), 7.94 (d, J=7 Hz, 1H), 7.56 (m, 2H), 4.37 (br peak, 2H), 1.84 (m, 2H), 1.71 (m, 1H), 0.93 (d, J=7 Hz, 6H)

Example 20

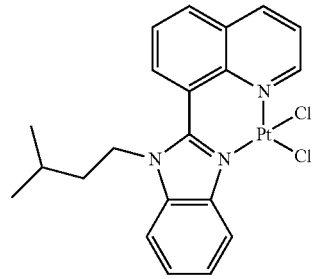

Prepared by following general procedures I, II and III.

¹H NMR (DMSO): δ 9.47 (dd, J=5, 1.5 Hz, 1H), 8.88 (dd, J=8, 1.5 Hz. 1H), 8.62 (d, J=6.5 Hz, 1H), 8.47 (m, 2H), 8.05 (dd, J=8, 7.5 Hz, 1H), 7.82 (m, 1H), 7.69 (dd, J=8.5, 5 Hz, 1H), 7.47 (m, 2H), 4.29 (br peak, 2H), 1.68 (m, 2H), 1.59 (m, 2H), 0.85 (d, J=6.5 Hz, 6H)

Example 21

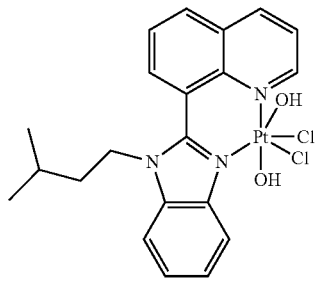

Prepared by following general procedures I, II, III and V.

¹H NMR (DMSO): δ 9.52 (dd, $J_{H-H}$=5.5 Hz, $J_{H-Pt}$=34.5 Hz, 1H), 8.96 (d, J=7 Hz, 1H), 8.73 (d, J=8 Hz, 1H), 8.53 (d, J=7 Hz, 1H), 8.47 (d, J=8 Hz, 1H), 8.05 (dd, J=8, 7.5 Hz, 1H), 7.98 (dd, J=8.5, 5.5 Hz 1H), 7.87 (d, J=8.5 Hz, 1H), 7.51 (m, 2H), 4.48 (br peak, 1H), 4.25 (br peak, 1H), 1.81 (br m, 1H), 1.72 (m, 2H), 0.89(br s, 6H)

Example 22

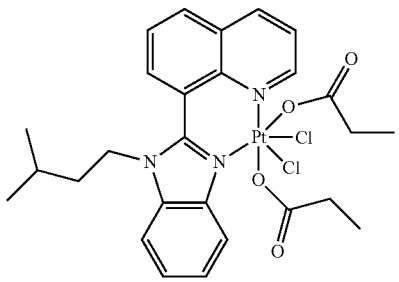

Prepared by following general procedures I, II, III, V and VI.

$^1$H NMR (DMSO, 80° C.): δ 9.54 (dd, $J_{H-H}$=5.5 Hz, $J_{H-Pt}$=31 Hz, 1H), 8.91 (dd, J=8.5, 1 Hz, 1H), 8.65 (d, J=8.5 Hz, 1H), 8.62 (dd, J=7.5, 1 Hz, 1H), 8.48 (d, J=8 Hz, 1H), 8.05 (dd, J=8, 7.5 Hz, 1H), 7.93(dd, J=8, 5.5 Hz 1H), 7.86 (d, J=8.5 Hz, 1H), 7.48 (m, 2H), 4.52 (t, J=8 Hz, 2H), 1.87 (br peak, 4H), 1.50 (m, 3H), 0.76(d, J=5.5 Hz, 6H), 0.55 (t, J=7.5 Hz, 6H)

ESI-MS (CH$_3$CN—H$_2$O, +ve mode): m/z 728.1

$^{195}$Pt NMR spectra were recorded on a Varian INOVA-400 spectrometer with K$_2$PtCl$_4$ (D$_2$O) at −1630 ppm as an external standard.

Biological Data

TABLE 1

| Example No. | Structure |
|---|---|
| 1 | 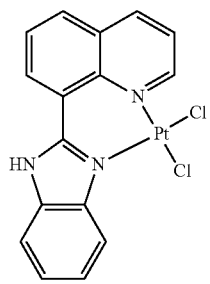<br>MW: 526 |
| 2 | 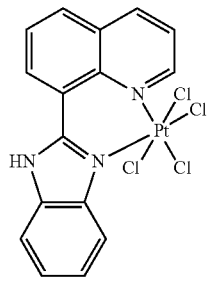<br>MW: 582 |

TABLE 1-continued

| Example No. | Structure |
|---|---|
| 3 | 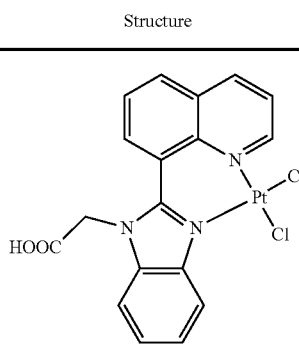<br>MW: 569 |
| 4 | 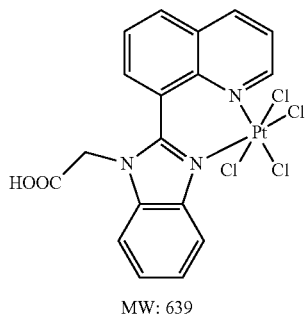<br>MW: 582 |
| 5 | 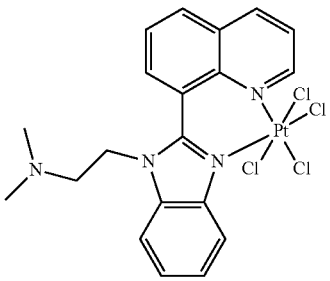<br>MW: 639 |
| 6 | MW: 652 |

TABLE 1-continued
| Example No. | Structure |
|---|---|
| 7 | 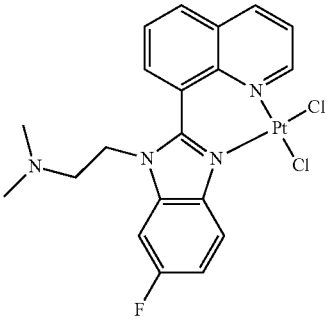 MW: 600 |
| 8 | 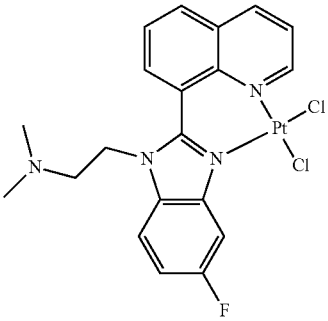 MW: 600 |
| 9 | 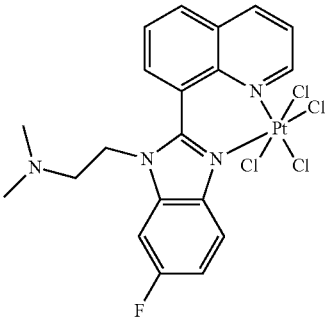 MW: 671 |
| 10 | 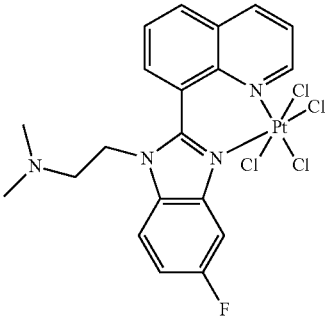 MW: 671 |
| 11 | 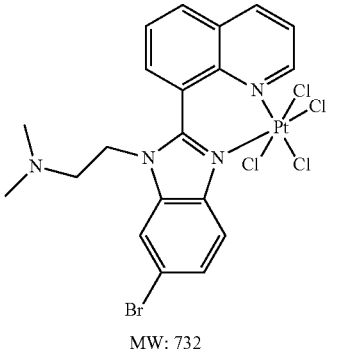 MW: 732 |
| 12 | 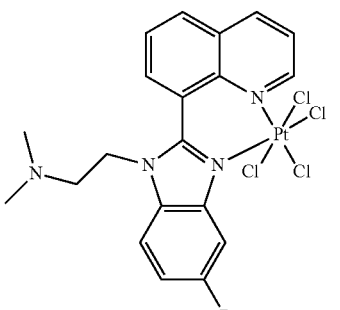 MW: 732 |
| 13 | 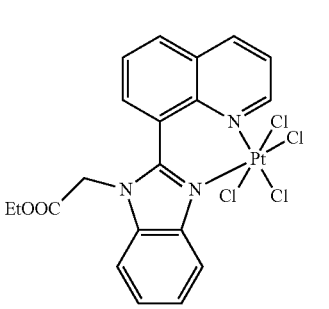 MW: 668 |
| 14 | 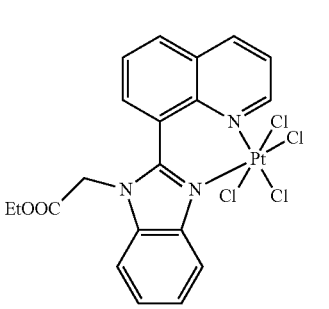 MW: 649 |

TABLE 1-continued
| Example No. | Structure |
|---|---|
| 15 | 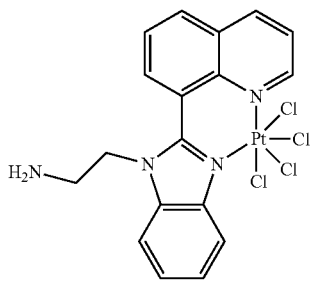<br>MW: 625 |
| 16 | 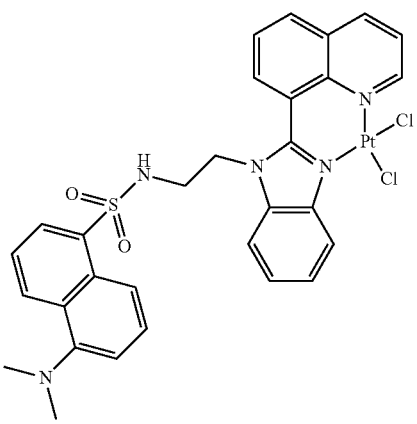<br>MW: 787 |
| 17 | 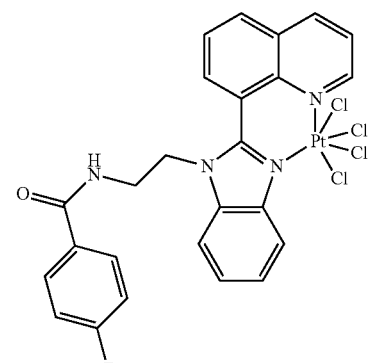<br>MW: 747 |
| 18 | 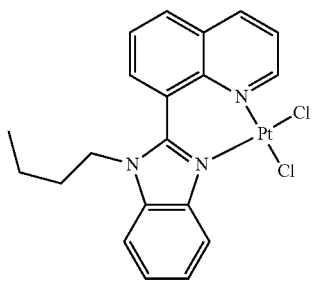<br>MW: 567 |
| 19 | 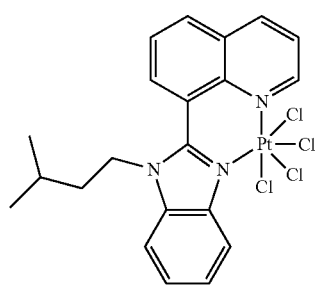<br>MW: 652 |
| 20 | 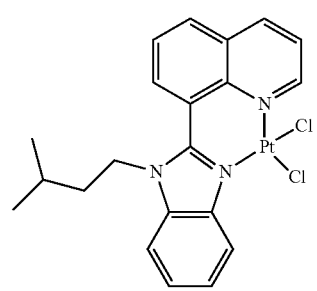<br>MW: 581 |
| 21 | 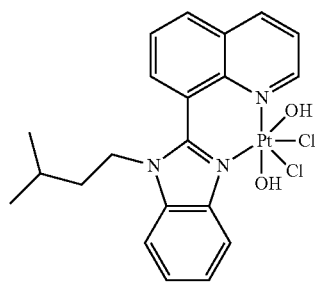<br>MW: 615 |
| 22 | 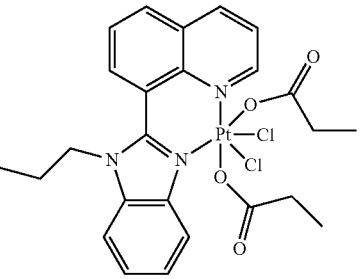<br>MW: 727 |

TABLE 1-continued

| Example No. | Structure |
|---|---|
| 23 | (structure shown) MW: 788 |

(i) Inhibition of Amyloid Formation:

This assay indicates whether the platinum compound (drug) can inhibit Abeta aggregation. Abeta was incubated with free ligand and its platinum complex Example 4 with/without Cu at 37° C. for 24 h to 48 h in PBS buffer. The result shows a dose response for Example 4 as shown in FIG. 1. Inhibition data for other compounds of the present invention are shown in Figures X and X.

(ii) Inhibition of Dityrosine Formation—'CuTy' Assay:

The CuTy assay is a Western blot assay which evaluates the ability of a test compound to inhibit the metal-mediated cross-linking reaction which leads to the formation of dimeric and higher order oligomers of Aβ. The assay models the process by which a putative agent acts either to compete with Aβ for redox active metals or alternatively to displace such metals by binding competitively at the Aβ metal binding site.

Figure 2:
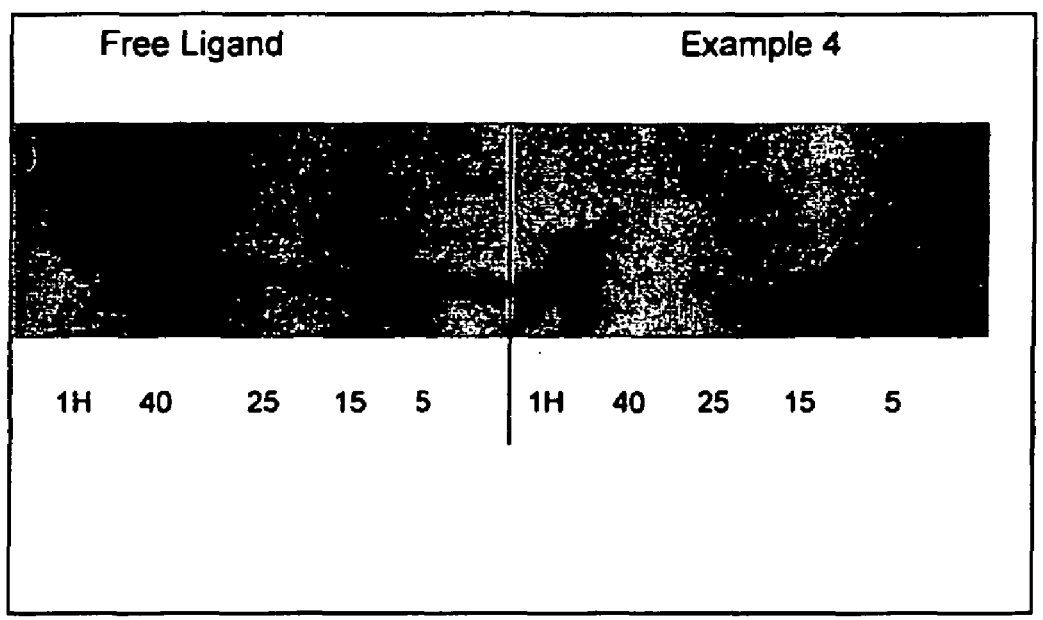
FIG. 2 is a gel photograph showing the inhibition of dityrosine formation comparing a metal complex (Example 4), against no inhibition as a free ligand. Data is presented as visual existence of gel bands.

If the metal binding site of Abeta peptide is blocked with a competitive affinity binder this should inhibit the formation of dityrosine peptide (dimer of Abeta). In this assay, generation of dityrosine cross links were observed by incubating Abeta (1-42) monomer (10 μm) in the presence of $H_2O_2$ (250 μm), $CuCl_2$ (25 μm) in PBS buffer with Example 4 and its free ligand. The reactions were incubated with slow rotation for 24 h at 37° C. and then quenched by addition of EDTA to complete the reaction. Dityrosine cross links were measured with western blot using the 1C3 antibody which is specific for the dityrosine moiety. FIG. 2 demonstrate the effect of Example 4.

Protocol for Oligomerisation:

Materials:

Aβ 1-40/1-42 (from Keck Laboratory); HFIP (from Sigma-Aldrich, Cat #105228); $CuCl_2$ (from BDH laboratory supplies, Cat #100884E; Gylcine (from Ajax Finechem, Cat #A1083; L-ASCORBIC ACID (Sigma Cat #A-0278; PBS (from Sigma, Cat #D8662); DMSO (from Ajax Finechem Cat #A2225; NaOH (from Sigma Cat #S-5851; 2-Mercaptoethanol (Sigma, Cat #M-7154; Tris (from BDH Cat #103157P); Tricine (SigmaCat #T-5816); SDS (from Bio-Rad Laborora-torias Cat #161-0302); ECL (from Amersham, Cat #RPN2106V1); Rabbit anti mouse Immunoglobulin HRP (from DAKO Cat #P0260); 10-20% Tricine Gel 10 wells (from Invitrogen Cat #EC6625 Box)

Stock Solutions:

Cu (II) (1 mM)-Gylcine (6 mM) solution in PBS; L-ASCORBIC ACID (5 mM) solution in PBS; NaOH (0.02M) solution in MQ $H_2O$; TBST: Tris buffer saline 0.1% Tween 20.

Analysis by Western Blot

Run samples on 10-20% gradient precast Tricine gel (4-12% Tris Glycine for A-11 antibody), (Novex). Running Buffer-Tris-Tricine (0.1 M Tris pH 8.25, 0.1 M Tricine, 0.1% SDS). Sample Buffer-4× (red); SDS 16%; Glycerol 60%; Tris 200 mM; Tricine 200 mM; Phenol Red 0.02%; 10% β-mercaptoethanol; Mix 30 ul of sample and 10 ul of 4× SB and boil for 5 mM; Load samples onto gel and run; Transfer onto nitrocellulose membrane; Transfer Buffer-25 mM Tris, 192 mM glycine, 20% methanol; After transfer, Boil membrane for 5 mins then block in 10% skim milk in TBST (0.01% Tween 20) for 1 hour at RT; Probe with primary antibodies* in 3% BSA/TBST (0.01% Tween20) at 4° C. O/N or 1 hour at RT; Wash three times 15 mM with TBST; Probe with secondary antibody-Goat anti-Rabbit IgG HRP (DAKO) 1 hour at RT; Wash three time 15 min in TBST; Develop blot using chemiluminescence reagents.

the primary antibody for detecting dityrosine is the antidi-tyrosine monoclonal antibody 1C3 [Kato, Y. et al (2000), Biochem. Biophys. Res. Commun. 275, 11-5.]

Oligomerisation can also be detected using generic antibodies which recognise full length Abeta and specific antibodies which are claimed only to detect soluble oligomeric forms of the peptide. (Lesne, S. et al (2006) Nature Vol 440116 March 2006|doi:10.1038/Nature04533).

Figure 3:
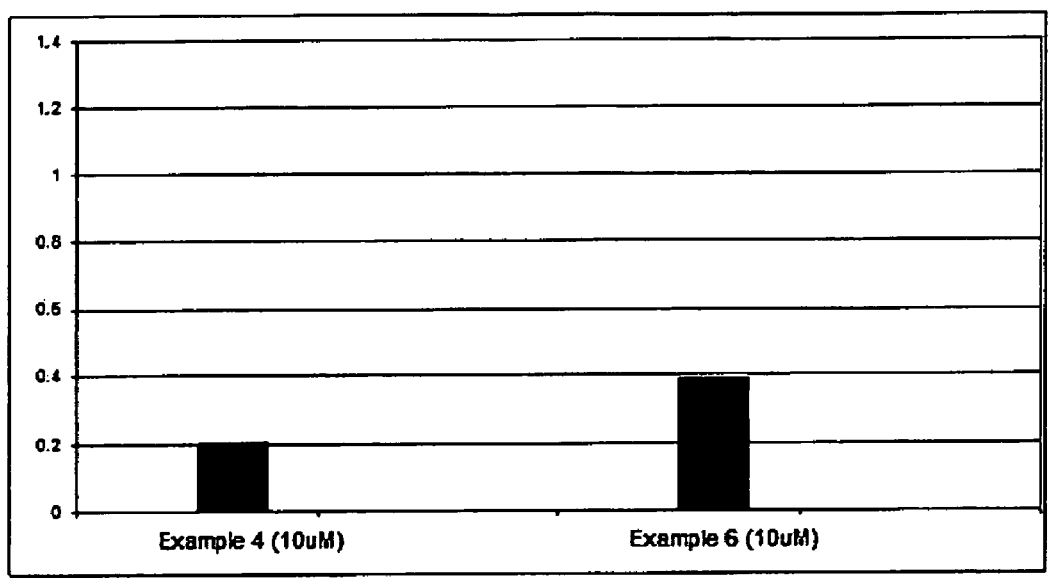
FIG. 3 is a bar graph showing concentration of each platinum complex (Examples 4 and 6) in M17 human neuroblastoma cells. Data is presented as µg/g of the test complex in the cell pellet sample.

(iii) Cytotoxicity:

Compound examples 4 and 6 were screened in a variety of cell lines including M17 and primary cortical neuronal cells to determine the toxicity of the platinum complexes. M17 human neuroblastoma cells were incubated with the compounds at 37° C. for 48 h. FIG. 3 shows the amount of each platinum complex compound found in the cell pellet in μg/g, establishing the ability of the compounds to cross the cell membrane. Platinum complex concentration was measured by ICP/MS and cell viability was measured to be >85% (high), establishing no cytotoxicity of the test compounds.

Cytotoxicty Protocol

Peptide and Example preparation: Example compounds were weighed using a microbalance. They were dissolved in DMSO (hybrimax) to an initial concentration of 50 mM then diluted to 4, 2 and 1 mM stock concentrations in DMSO. Drugs were kept in the dark till being added to Aβ. Aβpeptide was prepared as previously published (Ciccotosto JBC 2004). Briefly, Aβ was dissolved in 20 mM NaOH, diluted in water and finally in 10×PBS at a ratio of 2:7:1 parts. Peptide was sonicated in a water, centrifuged, and the peptide concentration determined by measuring the absorbance at OD214 and using a molar extinction coefficient to accurately calculate the concentration of the peptide.

Primary neuronal cultures: Cortical neuronal cultures were prepared as described previously (Ciccotosto, JBC 2004). Briefly, embryonic day 14 BL6Jx129sv mouse cortices were removed, dissected free of meninges and dissociated in 0.025% (w/v) trypsin. Dissociated cells were plated in poly-L-lysine coated sterile 48 well culture plates at a density of 150,000 cells/$cm^2$ in plating medium (MEM/10% FCS/5% HS). Cultures were maintained at 37° C. in 5% $CO_2$ for 2 h before the plating medium was replaced with Neurobasal growth medium containing B27 supplements. This method resulted in cultures highly enriched for neurons.

Setting up the cytotoxicty experiment: At 6 DIV, drug compound was co incubated with or without Aβ peptide for 2 to 10 minutes, diluted with fresh Neurobasal medium supplemented with B27 lacking antioxidants and mixed well. The existing culture media was discarded and the media containing Aβ and drugs added to the wells containing the cortical neurons. Each assay was done in triplicates, and the assay was repeated two times.

Cell viability assays: Cell survival was monitored by phase contrast microscopy and cell viability quantitated using the MTS assay (Promega, Madison, Wis.). After 4 days of treatment, the experimental conditioned medium was replaced with fresh Neurobasal medium supplemented with B27 lacking antioxidants and 10% v/v MTS added to each well. The plates were then incubated for 3 hr at 37° C. in 5% $CO_2$. 150 µL of the 200 µL media was transferred to a 96 well plate and any colour change in each well was determined by measuring the absorbance at 490 nm using a Wallac Victor Multireader and background readings of MTS incubated in cell-free medium were subtracted from each value before calculations. The data was normalized and calculated as a percentage of untreated vehicle control values. Data are shown as mean+/−SEM.

Figure 4:
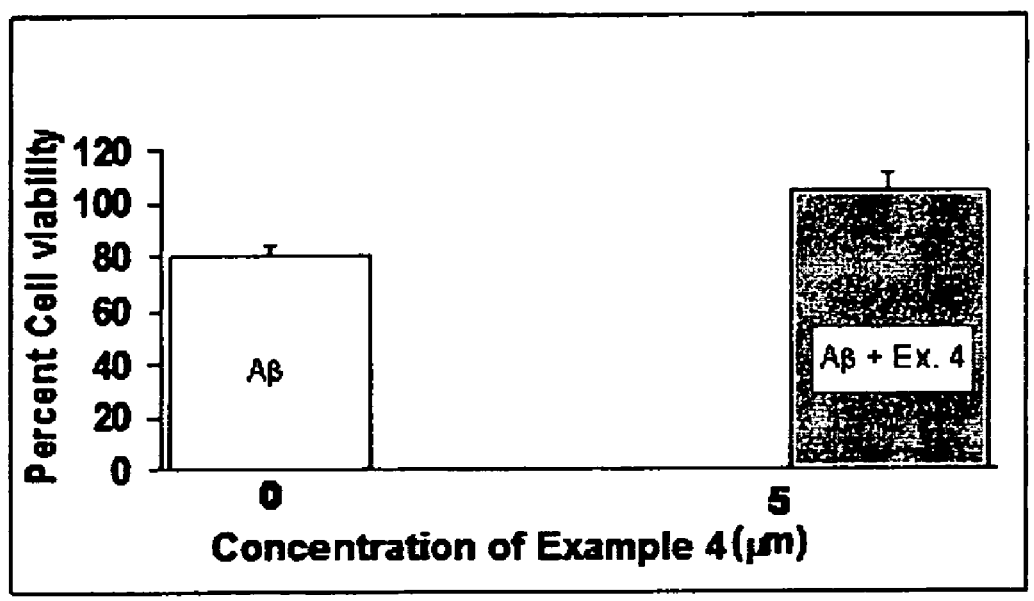
FIG. 4 is a bar graph showing viability of primary cortical neurons in the presence of Abeta and neuroprotection by Example 4. Data is presented as a percent of cell viability in the presence of Abeta alone and also Abeta plus compound.

(iv) Neuroprotection:

As Abeta is toxic to neuronal cell culture, the ability of platinum complexes to inhibit this toxicity was measured in the neuroprotection assay. In this assay primary cortical neurons isolated from mouse embryos (E14) were cultured for 6 days and then they were treated with Abeta peptide and Abeta in the presence of Example 4 at 37° C. for 4 days. Aβ was prepared by initially dissolving in 20 mM NaOH to a concentration of 1mM and sonicated for 5 minutes. The peptide was then diluted in $H_2O$ and 10×PBS to a final concentration of 200 uM Aβ in 1×PBS. The peptide was again sonicated for 5 minutes and then spun at 14000 rpm for 5 min and transferred to a fresh tube. The experiment was done in triplicate. The ability of the drug to rescue the toxicity of Abeta was measured using MTS reading and the results are shown in the FIG. 4.

Figure 5:
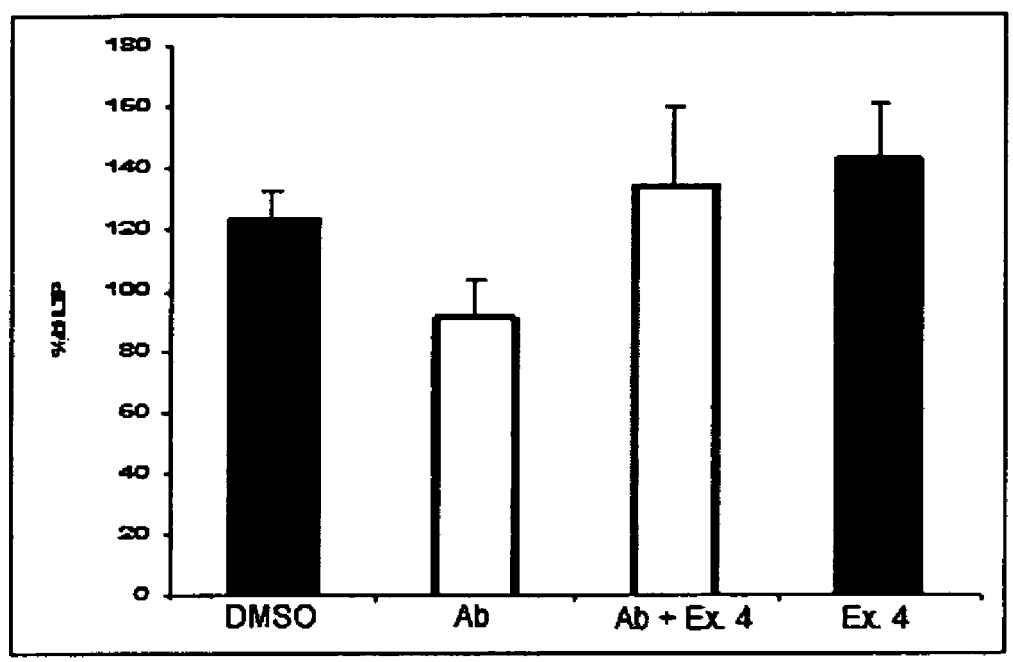
FIG. 5 is a bar graph showing the ex vivo long term potentiation (LTP) of mouse brain cells. Data is presented as a percentage of LTP and the rescue of toxicity induced by Abeta in the presence of Example 4.

(v) Long Term Potentiation (LTP) Studies:

This in vitro assay determines Abeta modulation of long term potentiation as a model for Abeta synaptotoxicity in AD. Example 4 has been studied in this assay and found that the platinum complex is rescuing the toxicity induced by Abeta, as shown in the FIG. 5.

In this assay, 14 to 40 day old C57B16 mice were decapitated under anesthesia by halothane inhalation in accordance with the University of Melbourne animal ethics guidelines. Brains were rapidly removed and chilled in ice cold artificial cerebral spinal fluid (ACSF). ACSF contained (in mM): 124 NaCl, 2.5 KCl, 2 $MgSO_4$, 2 $CaCl_2$, 10 D-glucose, 1.25 $NaH_2PO_4$, 26 $NaHCO_3$, and was gassed with 95% $O_2$/5% $CO_2$ (pH 7.35, HCl/NaHCO3). Abeta42, and cisplatin were dissolved in DMSO and administered to slices by a 30 minute pre-incubation in ACSF vehicle with DMSO levels controlled at 0.3%. All experiments were interleaved and conducted at room temperature. Field potential recordings were made in 350 µm transverse sections of the hippocampus by stimulating and recording in the stratum radiatum of the CA1 region. Recordings were made with an NPI microelectrode amplifier in bridge-mode, connected to a 20× preamplifier with 10 kHz low-pass 8-pole Bessel filtration (Krohn-Hite Corp. model 3381 filter/amplifier). Signals were digitized with a Digidata 1322A A/D converter (Axon Instruments) and stored on the hard drive of a personal computer using pClamp 8.2 or 9.0 software (Axon Instruments). Baseline stimulation intensity was calibrated at the beginning of each experiment to produce responses of 20-30% of the maximum slope of the fEPSP. Tetanic stimulation was a 1 second 100 Hz pulse delivered at the test intensity in substitution for the test stimulus. Data was analyzed offline using pClamp 8.2, Microsoft Excel and GraphPad Prism 3.03 software. The slope of each field excitatory post synaptic potential (fEPSP) was determined by linear regression of the data points between the peak of the pre-synaptic fiber volley and the peak of the fEPSP. Normalized fEPSP slopes were expressed as the percent of the average slope of the baseline between 30 to 20 minutes prior to tetanus. Long term potentiation was quantified by averaging the normalized data from 55 to 60 minutes post tetanus for each slice. Results were presented as the means+/−the standard error and statistical significance was determined using an unpaired t-test at the 95% confidence interval.

Experimental Treatment Protocol for Brain Slices

Slices were transferred to a 24 well plate and pre-incubated in gassed ACSF at room temperature with or without experimental compounds for 30 minutes immediately prior to electrophysiological recording. Abeta42 was dissolved in HFIP, dried, re-suspended in DMSO, and stored in small aliquots at −20° C. Abeta42 aliquots were rapidly thawed and used immediately. Abeta42 (3) and cisplatin was dissolved in DMSO immediately prior to use. Final DMSO concentrations were controlled at 0.3% in all pre-incubations.

(vi) Reduction of Tau Phosphorylation

The microtubule-associated protein tau is highly soluble under physiological conditions. However, in tauopathies, tau protein aggregates into insoluble filaments and neurofibrillary tangles (NFTs).

Tauopathies include a clinically diverse group of sporadic and familial neurodegenerative disorders in which filamentous, intraneuronal tau aggregates constitute a hallmark pathological lesion. Tau proteins are microtubule-associated proteins that promote microtubule assembly and confer stability to the microtubule network (Weingarten M D, Lockwood A H, Hwo S Y, Kirschner M W (1975) A protein factor essential for microtubule assembly. Proc Natl Acad Sci USA 72: 1858-1862; Cleveland D W, Hwo S Y, Kirschner M W (1977) Purification of tau, a microtubule-associated protein that induces assembly of microtubules from purified tubulin. J Mol Biol 116: 207-225.). In tauopathies, abnormally hyperphosphorylated tau polymerizes into straight filaments and paired helical filaments (PHFs), which aggregate to form neurofibrillary tangles (NFTs). The progressive accumulation of tau protein in tauopathies such as Alzheimer's disease (AD) and progressive supranuclear palsy (PSP) implicates tau as a factor in neurodegeneration.

Figure 6:
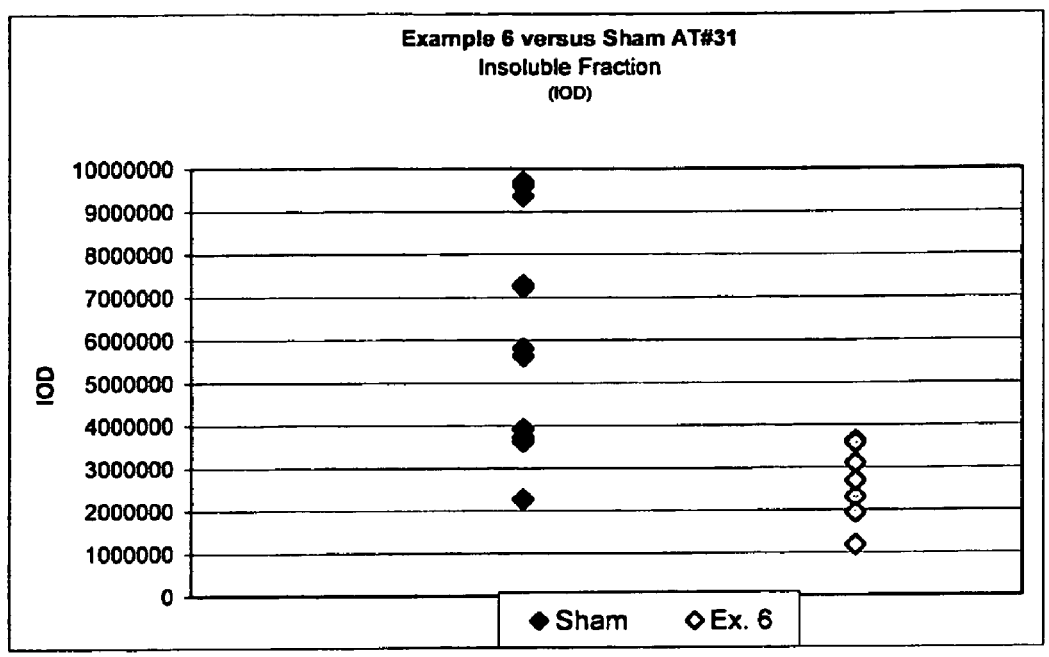
FIG. 6 is a graph showing the reduction of the insoluble fraction of Tau protein compared to shams. Data is presented as the Integrated Optical Density (IOD) or each fraction. The compound is designated as Example 6 and is defined in the specification.
Figure 7:
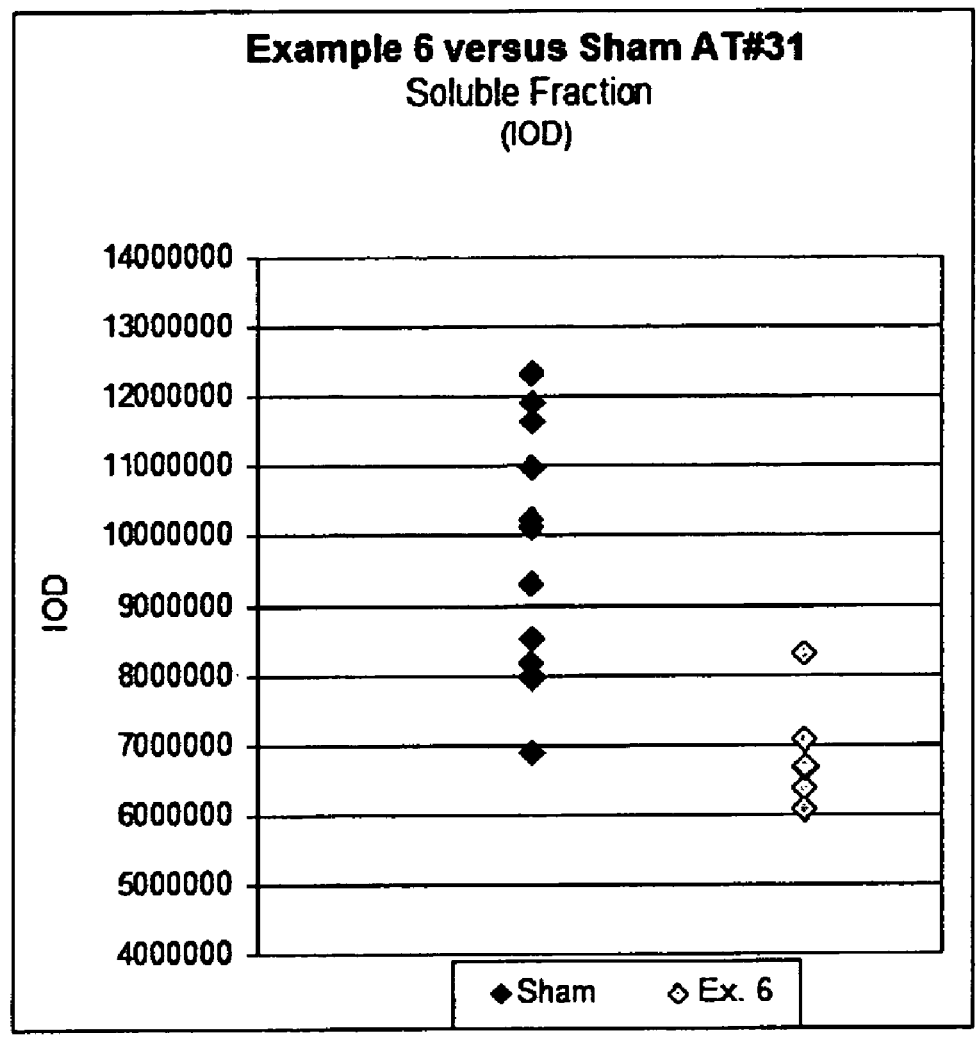
FIG. 7 is a graph showing the reduction of the soluble fraction of Tau protein compared to shams. Data is presented as the Integrated Optical Density (IOD) or each fraction. The compound is designated as Example 6 and is defined in the specification.

The data shown in FIG. 6 shows that treatment of transgenic mice with compound Example 6. Hyper-phosphorylation of tau is another biomarker of AD and is thought to be responsible for the cognitive deficits associated with AD. FIG. 6 shows the insoluble fraction. FIG. 7 shows the soluble fraction.

Tau Level Protocol:

The objective of this protocol is to compare the levels of Soluble (SN) and insoluble (pellet) Total tau and Phospho-Tau serine-396 from Treatment group compared to the Vehicle group.

Tissue Preparation

Brains were weighed before being frozen (wet weight). 1 ml of ice-cold PBS pH7.4 (50 ml PBS containing 1 EDTA-free protease inhibitor tab) was added per brain. Brains were sonicated on ice for 2×~15 sec bursts at 40% intensity, or until they appeared homogenised. Samples were spun at 100,000 g, 4° C. for 30 min, supernatant was collected and aliquoted. The same volume was added to each respective sample as for the first homogenisation step, then sonicated the same way as described. Pellet was then also aliquoted accordingly.

Determination of Protein Levels for All Samples:

The BCA assay kit (Pierce) was used to determine the protein concentration of the pellet and SN samples.

A 20 ul aliquot of Pellet and SN were diluted 1:10, i.e. added 180 ul of PBS.

Determined protein concentration as per BCA assay method. The Absorbance levels were around the 0.1-1.5 Abs. Using the excel program determined the volume of PBS required to make a stock solution of 4.5 ug/ul of protein of SN and a 0.3 ug/ul of protein of Pellet using the 20 ul aliquots.

Preparation of Samples for Western Blotting:

Once the protein content of each sample was determined by the BCA assay a 4.5 ug of protein/ul sample of SN and the 0.3 ug of protein/ul sample of pellet was prepared. A 10ul aliquot of the 45-ug/ul stock solution of the SN and the 0.3-ug/ul stock solution of the pellet was taken to make up a 45 and 3 ug protein/lane sample, respectively. Added 10 ul of SBx4 (diluted to x2 with dH2O) containing 10% mercaptoethanol to each 10 ul sample.

Heated the samples for 10 min at 90° C. Pulse spun the samples for ~10 sec. Loaded samples on 4-12% Bis-tris gels, 20 well gels (Criterion Gel, BioRad). Ran gels @ 115V for 10 min then 180V 45 min (phospho tau 11 Nov. 07) and 120V 72 min then 180V for 26 min for total tau (19 Nov. 07) in MES buffer at rm temp. Transferred gels using iblot program 3 for 6 min. Heated membrane for 5 mins in 1×PBS (preheated) in microwave. Blocked membrane 1 h in 5% skim milk in TBST at room temp.

Probed with primary antibody 1 hr at 4° C. overnight: anti-total-Tau (anti-human raised in rabbit) (DAKO; 1:2000, 10 ul/20 ml per blot) in TBST, or anti-phospho-tau (pS-396; 10 ul/15 ml per blot in TBST). Next day washed blots ~6×10 min with TBST. Probed with secondary antibody for 1 hour at room temp: anti rabbit HRP (DAKO) 1:5000 diluted in TBST (4 ul/20 ml per blot). Further washed blots for 6×10 min with TBST. Used ECL reagent (Amersham) to develop blots (8 ml per blot, 1:1 ratio reagent A and B). Incubated the blots in ECL for 2 min.

All the membranes were captured using the "LAS-4000" (Fujifilm) image capturing system at 4 sec (auto) capture time at the super setting, except phospho tau pellet (30 s) super auto. The area appearing between ~49 and 62 kDa was quantitated using the Multi Gauge V3.0 software program. IOD (optical density) was used to compare treated and vehicle groups for relative levels of phospho-Tau or total-tau.

Performed statistical evaluation comparing vehicle versus treatment group using "t-Test: Two-Sample Assuming Unequal Variances" for IOD (Integrated Optical Density) for both pellet and SN samples. Also compared phospho tau:total tau ratio differences between vehicle and drug-treated animals.

(vii) Preparation of Imaging Agents—Method of Separation

Figure 8:
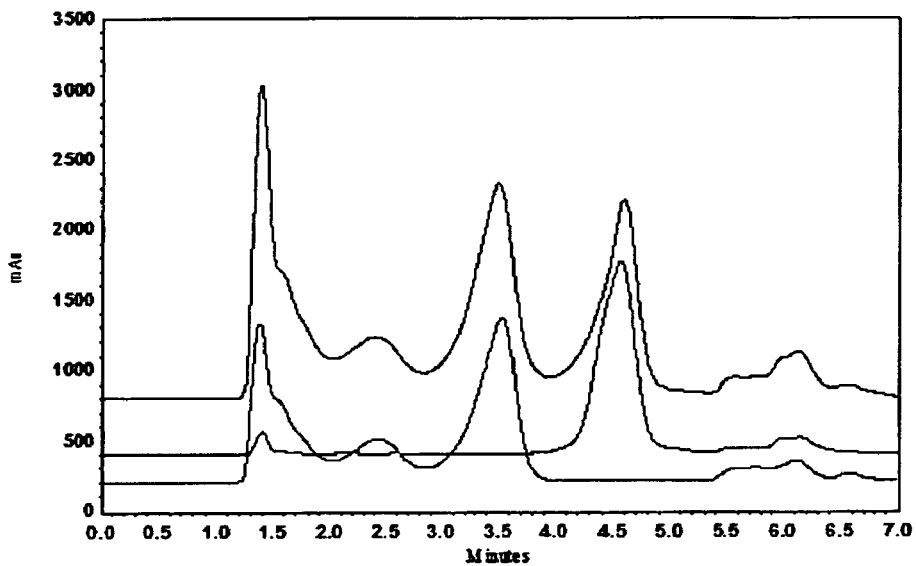
FIG. 8 is a graph showing the final radiolabeled compound (Example 9) separated from its precursor. Data is presented as levels of absorbance (at 275 nm) over minutes. The compound is designated as Example 9 from its precursor Example 11 and is defined in the specification.

In order to make a radiolabelled compound; a standard analytical HPLC method is implemented so that the final radiolabled compound can be separated from its precursor. FIG. 8 shows the HPLC separation of the final compound Example 9 from its precursor Example 11. Example 9 is cold with a F19 (standard) and hot with F18.

Figure 9:
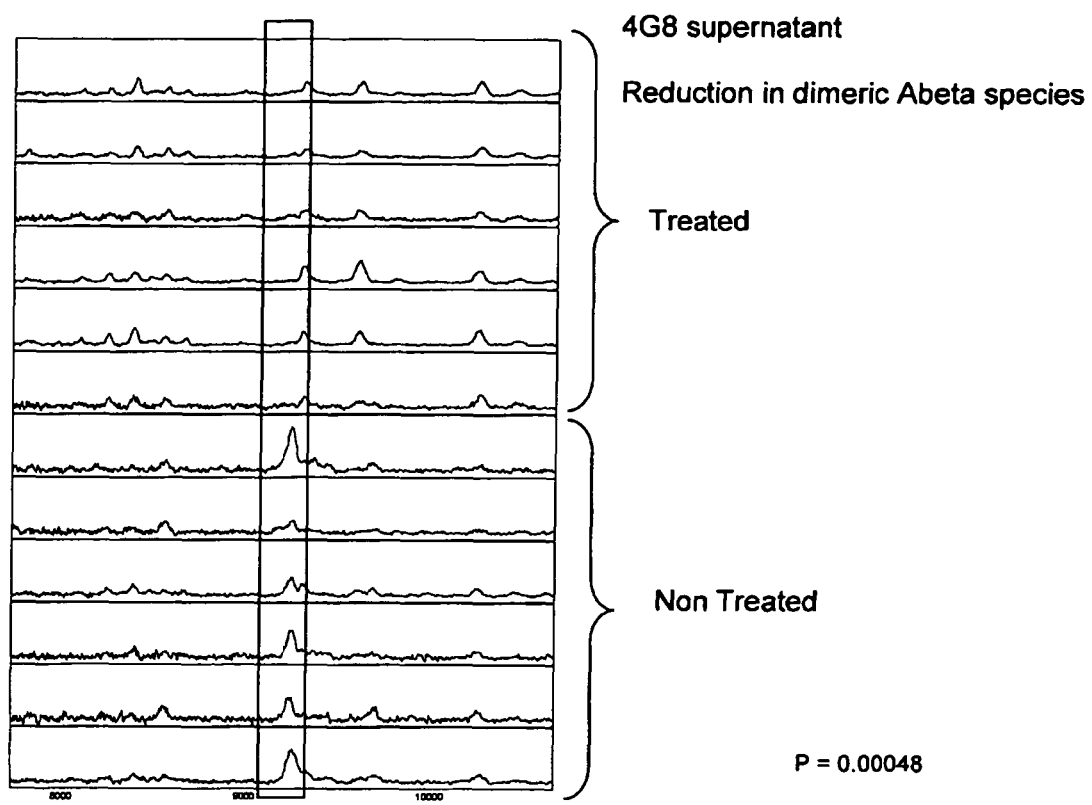
FIG. 9 is a graph showing existence of dimeric forms of Abeta protein. Data is presented as SELDI-TOF mass spectra data, with X axis figures providing mass in Daltons. The compound is designated as Example 6 and is defined in the specification.
Figure 10:
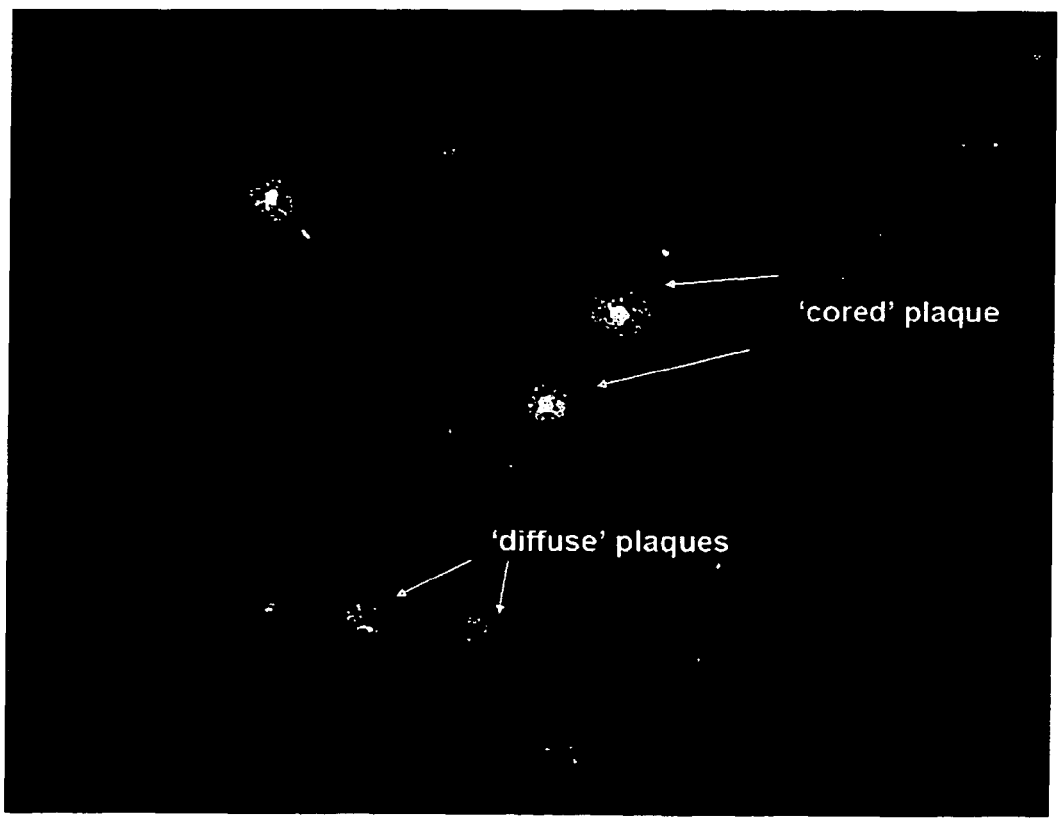
FIG. 10 is a PET image of human brain tissue stained with Example 16. Data is presented as fluoresence images of protein targeted by Example 16.
Figure 11:
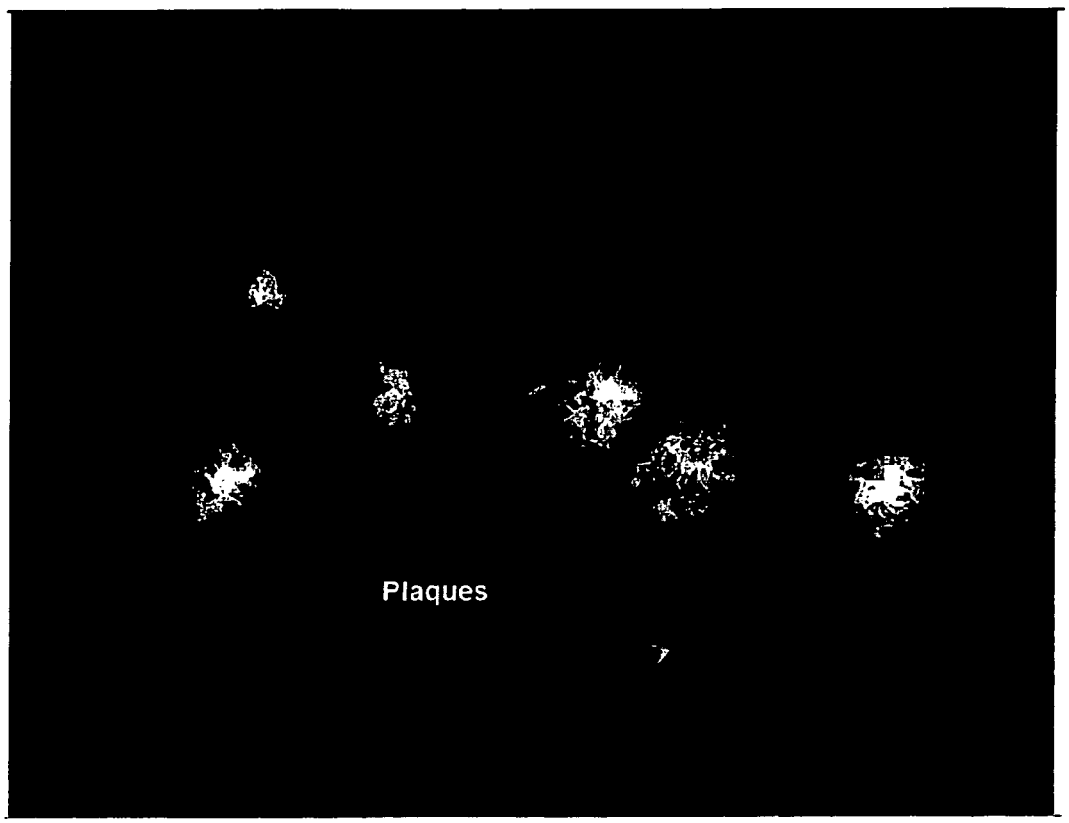
FIG. 11 is a PET image of human brain tissue stained with Example 16. Data is presented as fluoresence images of protein targeted by Example 16.
Figure 12:
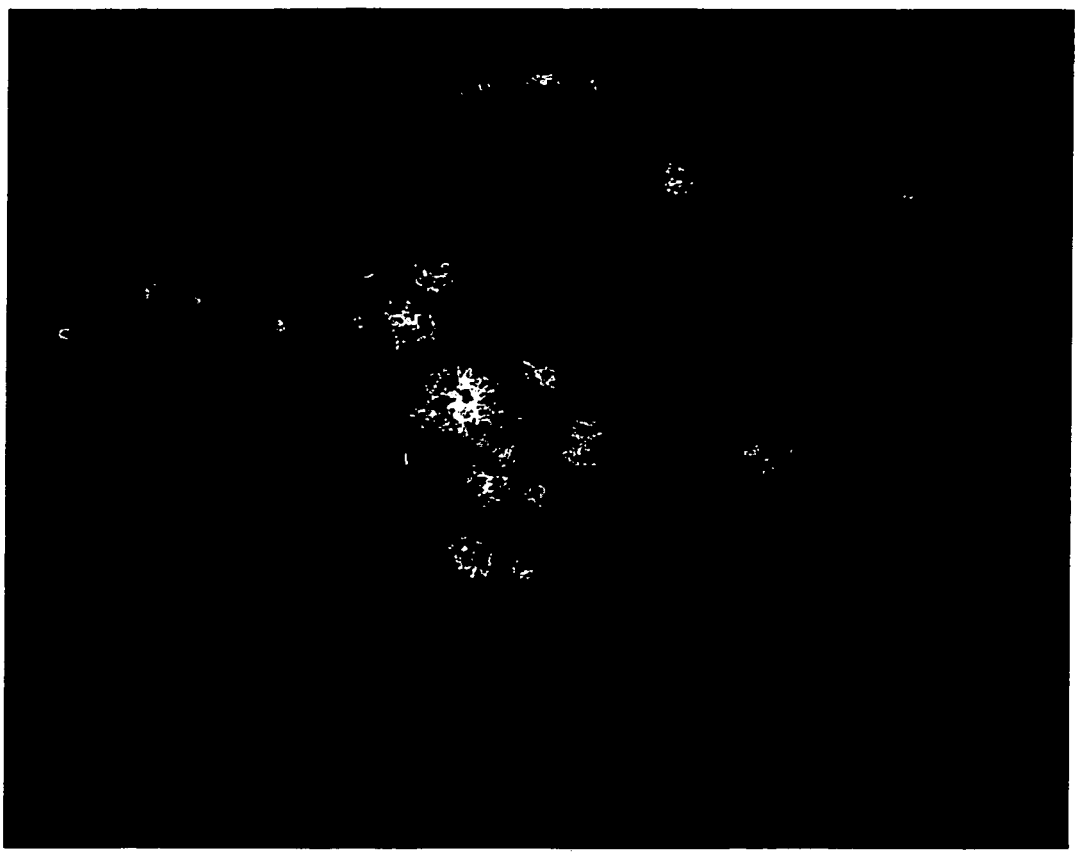
FIG. 12 is a PET image of human brain tissue stained with Example 16. Data is presented as fluoresence images of protein targeted by Example 16.
Figure 13:
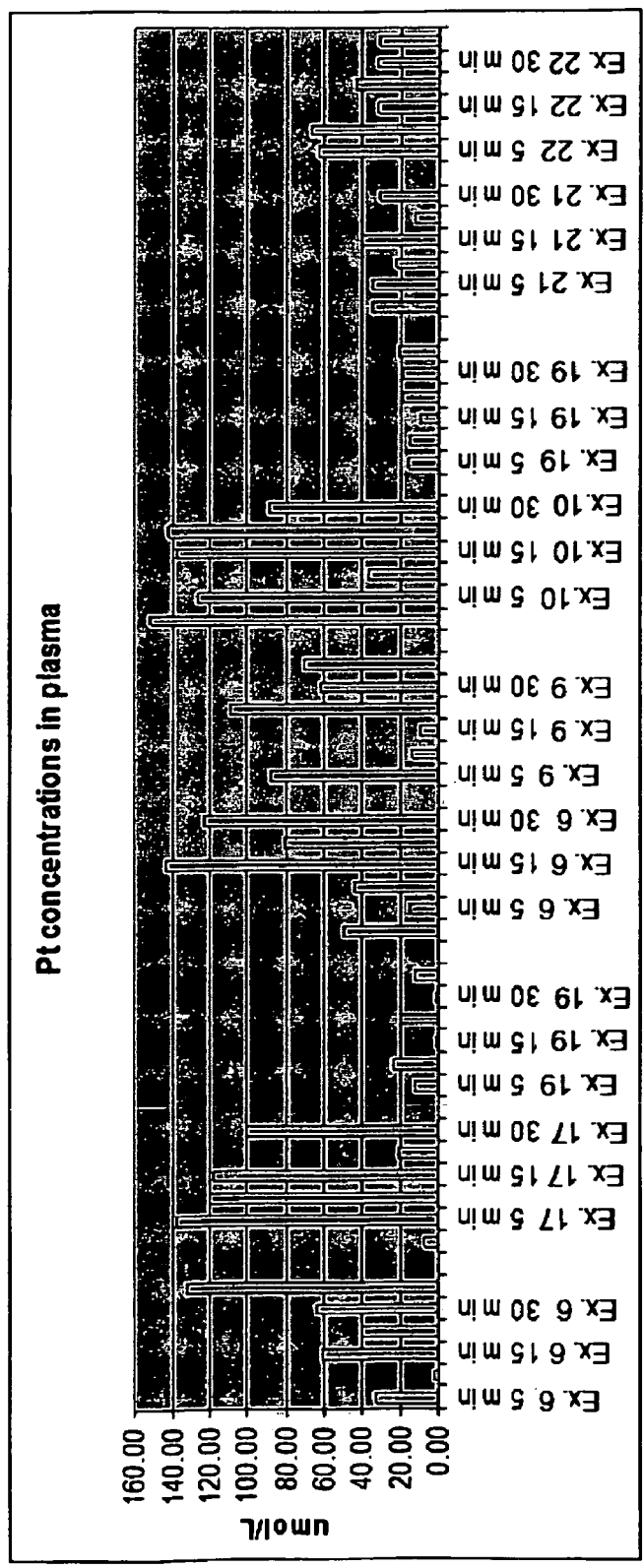
FIG. 13 is a graph depicting the concentration in plasma of exemplified compounds of the present invention.
Figure 14:
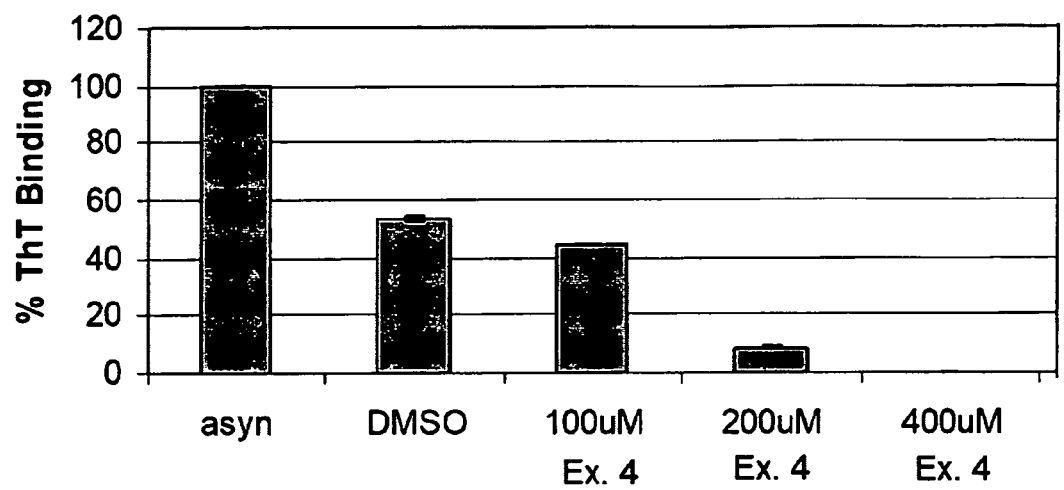
FIG. 14 is a graph showing inhibition of a-synuclein fibrils (% ThT binding vs concentration of Example 4).
Figure 15:
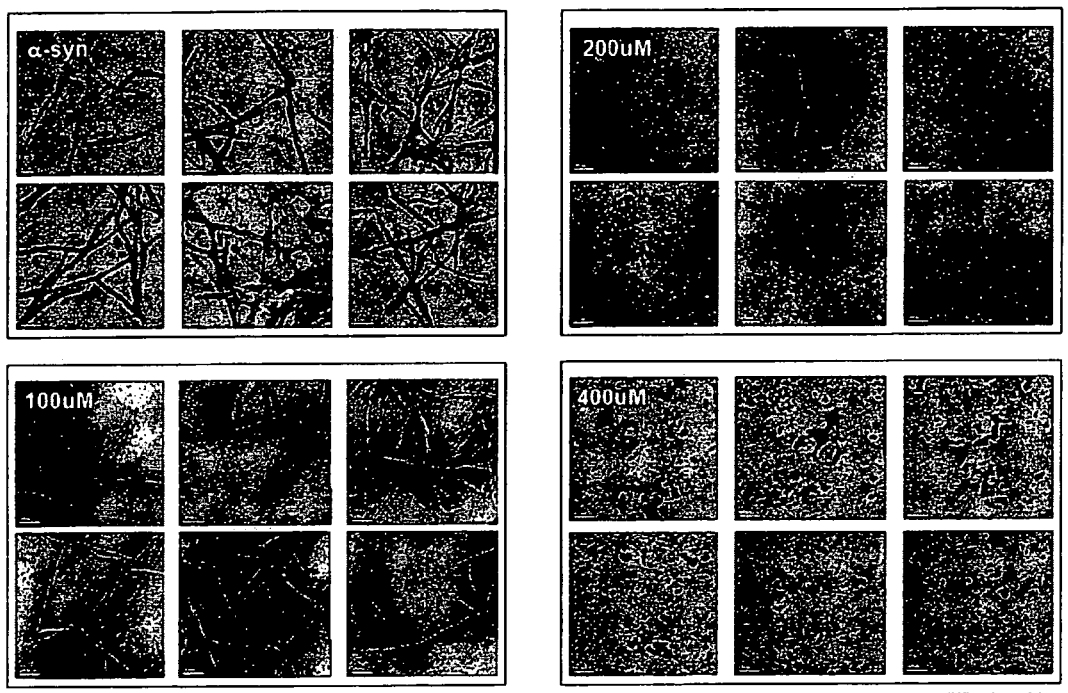
FIG. 15 is a series of EM images depicting breakdown of a-synuclein protein after a 5 day treatment with different concentrations of Example 4.
Figure 16:
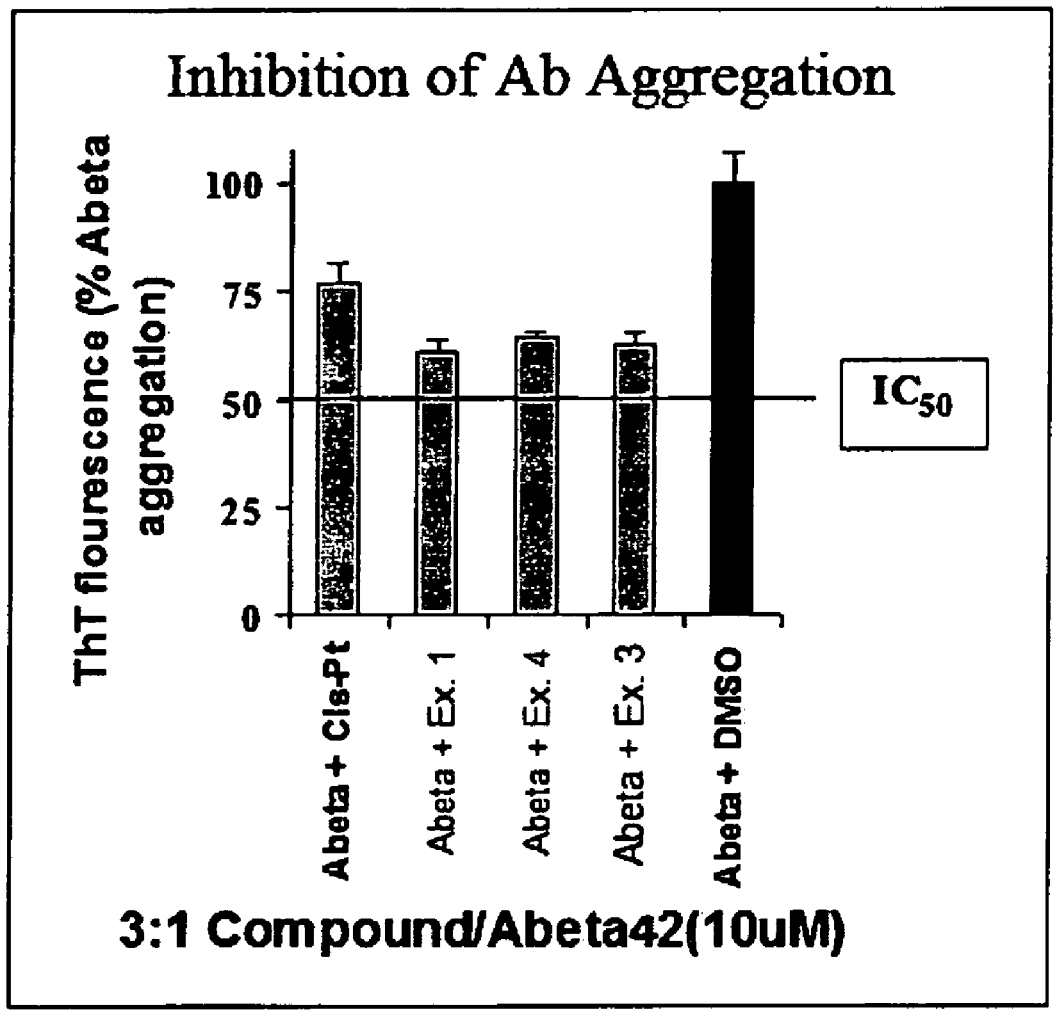
FIG. 16 is a graph depicting the inhibition of amyloid formation by test compound Examples 1, 4, and 3 (10 µM) at a 3:1 compound to Abeta ratio.
Figure 17:
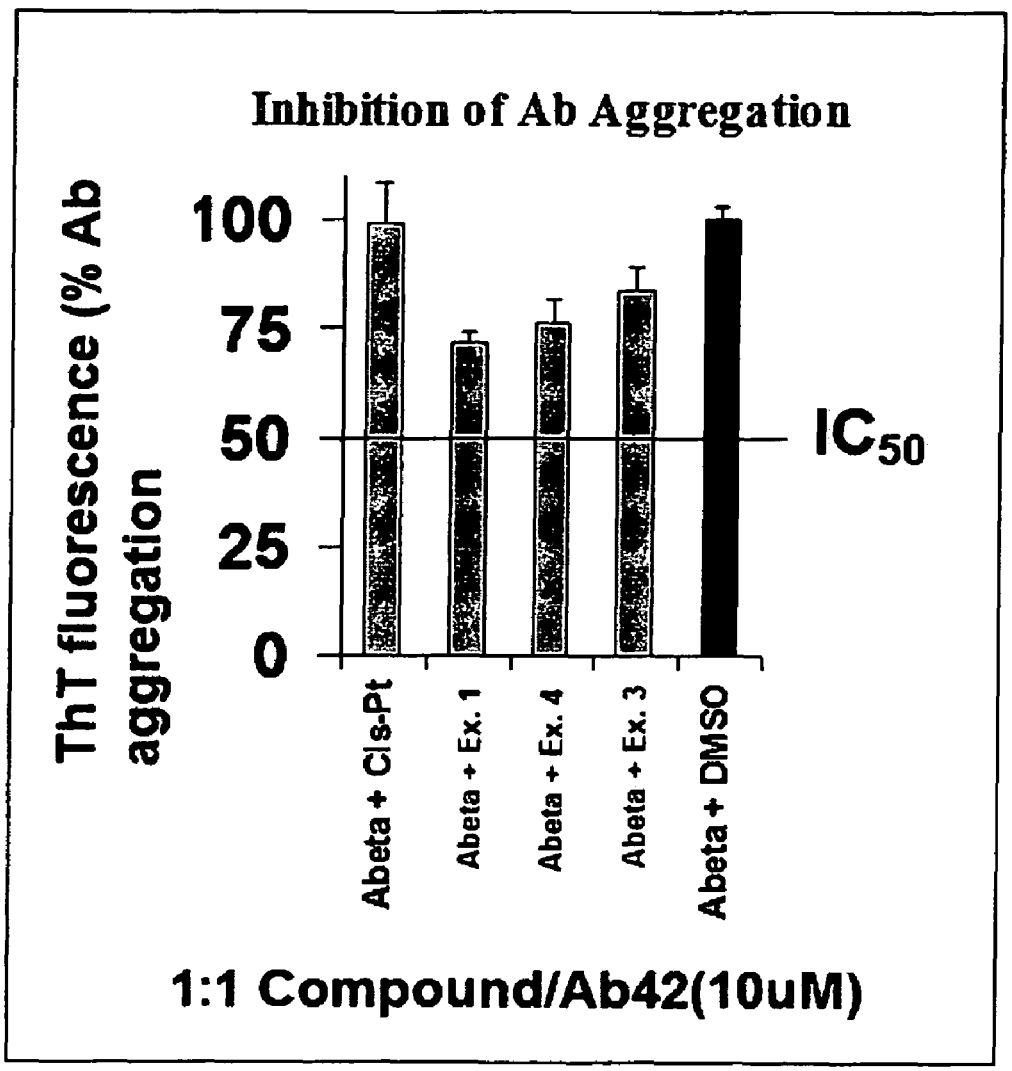
FIG. 17 is a graph depicting the inhibition of amyloid formation by test compound Examples 1, 4, and 3 (10 µM) at a 1:1 compound to Abeta ratio.
Figure 18:
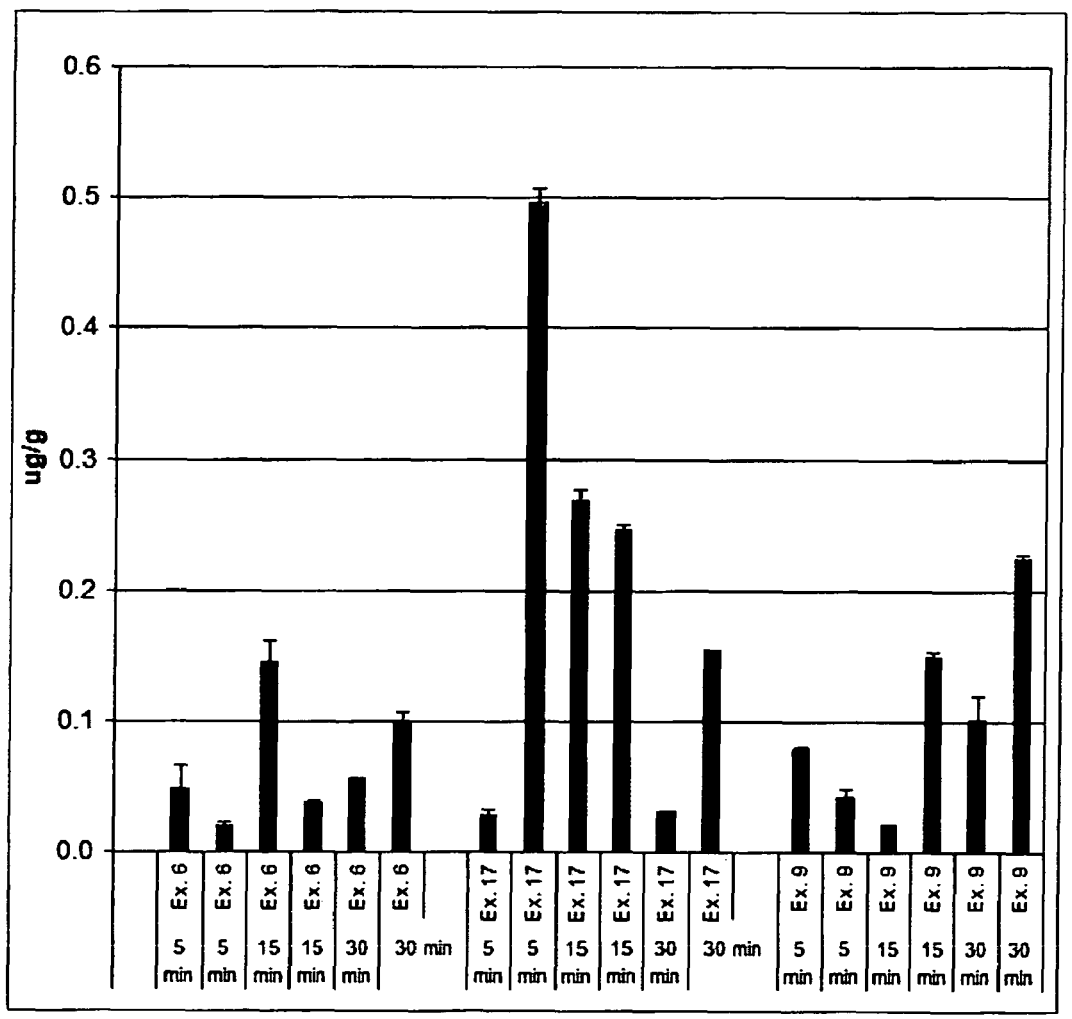
FIG. 18 is a graph depicting the concentration in the brain of exemplified compounds of the present invention.
Figure 19:
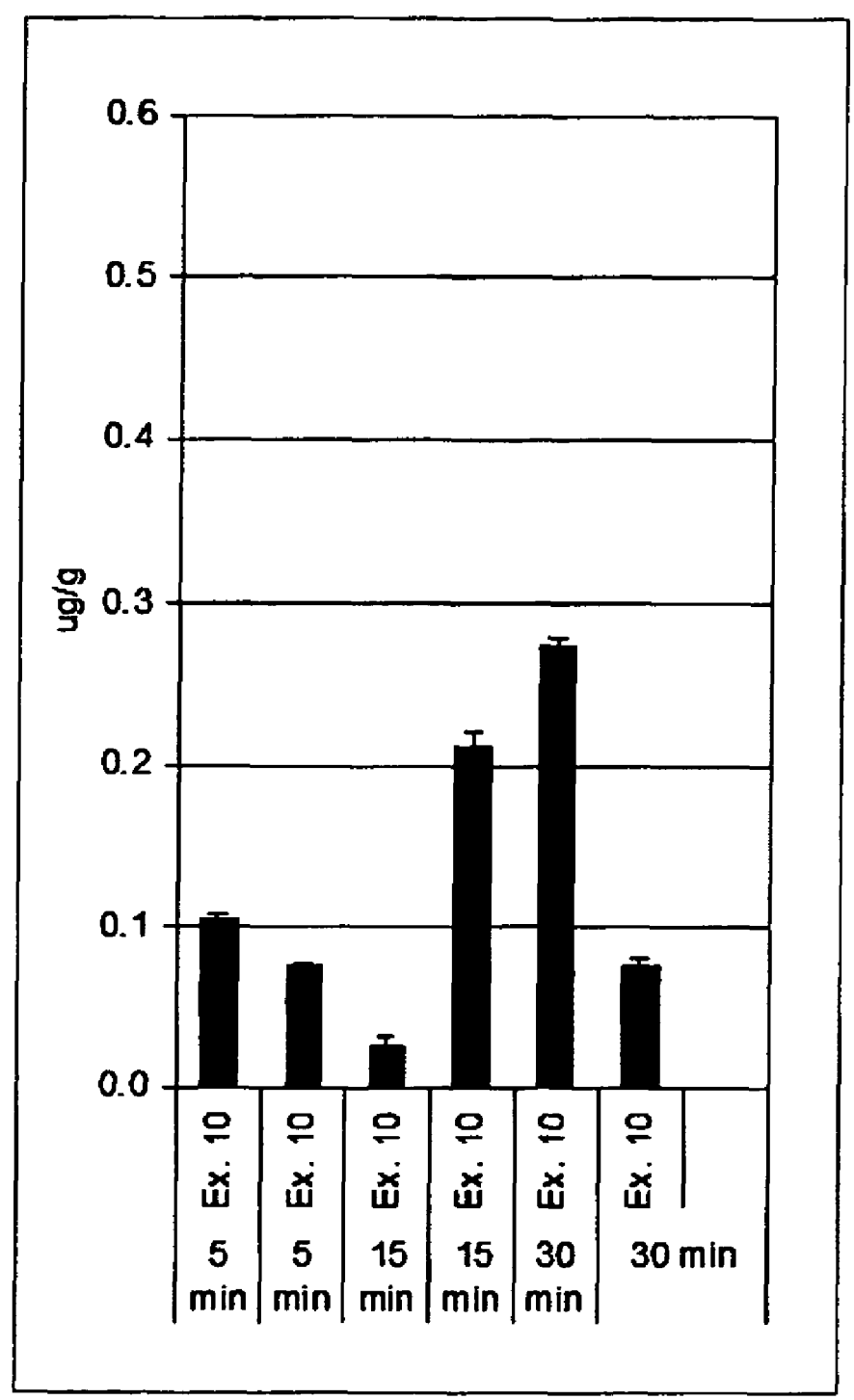
FIG. 19 is a graph depicting the concentration in the brain of exemplified compounds of the present invention.

(viii) In Vivo Mouse—Abeta Assay:

Example 6 has been trialled in the TG2576 mouse model of Alzheimer's disease. At the end of the trial the brains were collected and fractionated into soluble and insoluble fractions. These fractions were then analysed by SELDI-TOF mass spectra looking at biomarker changes in response to drug as shown in FIG. 9. Several changes were observed using the 4G8 antibody that targets APP/Abeta. The rectangle on the mass spectra above shows that in the supernatant fraction from non-treated animals there is a peak with a mass of 9260 Da a mass this is consistent with a dimeric form of Abeta. This peak is not present in the treated animals. The X axis figures are the mass in Daltons. The Mass region of the abeta dimer is identified above.

SELDI-TOF Protocol

PS 10 ProteinChip arrays were used, where a volume of 2 µl of antibody (4G8) in PBS (0.25 mg/mL) was added to each spot of the chips and IgG bovine as a negative control. The arrays were incubated in a humidity chamber at 4° C. overnight. The Antibodies were removed and blocking buffer (0.5M ethanolamine in PBS) was added (10 µL), the array was incubated for 60 min. The blocking buffer was removed and each spot was washed with 10 µL of 0.5% Triton X-100/ PBS (wash buffer) for 5 min. The solvent was removed and the spots were washed with 10 µL of PBS for 5 min. A volume of 15 µl of sample was added to each spot, the arrays were incubated at room temperature for 3 hours. The samples were removed and each spot was washed with 60 µL of wash-buffer twice for 10 sec, then a PBS wash was done 60 µL PBS twice for 10 sec and finally the arrays were washed with 60 µL 1 mM HEPES 1 mM twice for 10 sec. The arrays were air-dried. A volume of 1 µL of sinapinic acid (SPA, 50% saturated in 50% (v/v) acetonitrile and 0.5% in TFA) was applied to each spot twice. The array was air-dried between each application. All the incubations and washes were performed on a shaking table. Chips were analyzed in a PBSIIC, SELDITOF MS, and peaks were analysed using Ciphergen ProteinChip software 3.1.

The samples were treated as follows:

Pellet and supernatant were treated the same way: 60 µL of sample were mixed with 7.5 µL of Urea (8M) 10 µL of wash buffer and 10 µL of PB, 15 µL of that mixture were loaded per spot.

(ix) Bioavailability Protocol

Brain (and Liver & Kidney) Tissue:

Added x ml of Conc. Nitric Acid ($HNO_3$) (Aristar, BDH) to each lyophilised tissue and allowed them to digest overnight at room temperature Further digested the samples by heating 20 minutes at 90° C. using a heating block. Samples were then removed from the heating block and an equivalent volume of x ml of Hydrogen Peroxide ($H_2O_2$) (Aristar, BDH) was added to each sample. Samples were allowed to stop effervescing (digesting), ~30 minutes, before heating again for a further 15 mins at 70° C.

Determined the average reduced volume after digestion for the each type of tissue sample (referred to as Reduced Volume). Samples were diluted with a 1% nitric acid diluent in triplicate.

As controls, preparatory blank tubes (no tissue added) and Bovine liver 1577b NIST SRM (20 mg & 40 mg dry wt) were treated the same manner as the samples. See sheet "BL SRM".

X=0.4 ml for brain & kidney and 0.6 ml for Liver.

Brain Supernatant (SN) Samples:

When the SN (350 ul) aliquots were thawed out, there were was a lot of precipitates/clumps present in the samples. The samples had to be briefly pulse spun to pellet the precipitates in order for a soluble aliquot to be taken. From the SN (350 ul) tube, took 3×100 ul aliquots which were added to 900 ul of 1% nitric acid diluent (dilution factor 1/10), in triplicate.

Plasma Samples:

To the 80 ul aliquots of the plasma added 0.8 ml of 1% nitric acid diluent (dilution factor 1/11).

Measurements were made using a Varian UltraMass ICPMS instrument under operating conditions suitable for routine multi-element analysis. The instrument was calibrated using Blank, 10, 50 and 100 ppb of a certified multi-element ICPMS standard solution (ICP-MS-CA12-1, Accustandard) prepared in 1% nitric acid for Mn, Fe, Cu, Zn and Pt. Used an certified internal standard solution containing 100 ppb of Yttrium (Y 89) via a T-piece as an internal control (ICP-MS- IS-MIX1-1, Accustandard).

Results are expressed as micrograms of metal per gram of wet weight of tissue (ug/g) and for the plasma samples only as umol/l.

(x) PET Ligand Staining of Human Brain Tissue—Protocol

All procedures conducted at room temperature
Brain sections cut at 7 microns on micronmeter
Note procedure can be used for fresh frozen or formalin/paraffin fixed tissue; use applicable preparation of tissue steps and then follow 'Cont. Staining' procedure
For formalin/paraffin fixed tissue:
1. Place slides containing tissue sections in glass carriage and soak in Shellex solution for 2-3 mins (to be done three times)
2. Soak slides in 100% ethanol and incubate 2 mins
3. Soak slides in 90% ethanol and incubate 2 mins
4. Soak slides in 70% ethanol and incubate 2 mins
5. Soak slides in deionised water and rock for >2 mins
6. Change deionised water and repeat; keep sections moist at all times
7. Transfer section to humidity chamber
For fresh frozen tissue:
1. Thaw sections for 10 mins at room temp
2. overlay slides with deionised water in humidity chamber
Cont. staining
Set up humidity chamber. Ensure that tissues are pre-wetted and assemble bamboo sticks so as slides can layed on top
1. Transfer slides to humidity chamber and keep moist with water
2. Draw circle around tissue with Dako pen, to create hydrophobic barrier
Quenching of Autofluorescence
3. Bring sections to water.
4. 1×5 min wash in PBS.
5. 0.25% KMnO$_4$ (in PBS) for 20 min.
6. 2×2 min washes in PBS.
7. 1% Potassium Metabisulfite & 1% Oxalic Acid (in PBS) for 1-6 min until brown colour washes out.
8. 3×2 min washes in PBS.
Compound Staining (adapted from Kiunk).
9. 2% BSA (in PBS pH 7.0) for 10 min.
10. 100 uM Compound x (in PBS) for 30 min.
11. 2% BSA (in PBS) wash for 4 min.
12. 3×2 min PBS wash.
13. Dip in dH$_2$O.
14. Coverslip with Dako aqueous mounting medium (for fluorescence detection).
Microscopy Imaging
For PiB microscopy imaging—visualize under UV filter (365/420)
For VJ35 microscopy imaging, use the following filter sets:
47CFP=filter set 47 (EM BP 436/20, BS FT 455, EM BP480/40)*
365/80 nm
420/440
VJ35 best visualized using this filter set.

The claims defining the invention are as follows:
1. A transition metal complex of formula (I) or salts thereof:

wherein:
X is selected from a transitional metal consisting of Pt, Tc, Pd, Mn, Fe, Ru, Au, Re and Rh;
n is an integer from 2 to 6;
each $R_1$ is independently selected from halogen, NR'R"R''' (where each of R', R", and R''' is independently selected from hydrogen, alkyl, cycloalkyl, aryl, heteroaryl, heterocycyl and oxyacyl), optionally substituted acyloxy, optionally substituted alkoxy, SR'R" (where each of R' and R" is independently selected from hydrogen, alkyl, cycloalkyl, aryl, heteroaryl, heterocycyl and oxyacyl), optionally substituted heteroaryl, optionally substituted carbohydrate, or any two $R_1$ form a malonate, oxalate or glycolate;
$R_2$ is selected from optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and
wherein each $R_3$-$R_{10}$ independently represents H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or R₉ and R₁₀ together form an optionally substituted aryl, optionally substituted heteroaryl, or optionally substituted cycloalkenyl.

2. A transition metal complex according to claim 1 wherein one or two of R₃-R₁₀ are substituted.

3. A transition metal complex of formula (I') or a salt thereof;

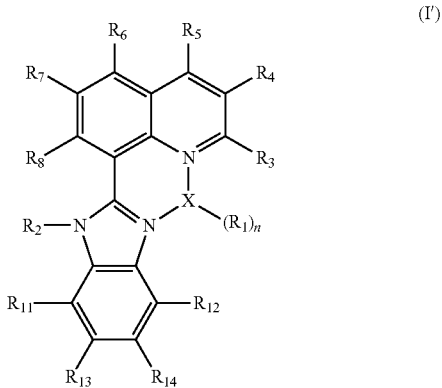

wherein:
X is selected from a transition metal consisting of Pt, Tc, Pd, Mn, Fe, Ru, Au, Re and Rh;
n is an integer from 2 to 6;
each R₁ is independently selected from halogen, NR'R"R'" (where each of R', R", and R'" is independently selected from hydrogen, alkyl, cycloalkyl, aryl, heteroaryl, heterocycyl and oxyacyl), optionally substituted acyloxy, optionally substituted alkoxy, SR'R" (where each of R' and R" is independently selected from hydrogen, alkyl, cycloalkyl, aryl, heteroaryl, heterocycyl and oxyacyl), optionally substituted heteroaryl, optionally substituted carbohydrate, or any two R₁ form a malonate, oxalate or glycolate;
R₂ is selected from optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and
wherein each R₃-R₈, and R₁₁-R₁₄ independently represent H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy.

4. A transition metal complex according to claim 3 wherein one or two of R₃-R₈ and R₁₁-R₁₄ of compounds of formula (I') are substituted.

5. A transition metal complex according to claim 3 wherein one of R₃-R₈ and R₁₁-R₁₄ of compounds of formula (I') is substituted.

6. A transition metal complex according to claim 3 wherein R₃-R₈ and R₁₁-R₁₄ in compounds of formula (I') represent hydrogen.

7. A transition metal complex according to claim 1 wherein R₂ is a substitutent group selected from optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl.

8. A transition metal complex according to claim 7 wherein R₂ is an optionally substituted C₁₋₇ alkyl.

9. A transition metal complex according to claim 7 wherein R₂ is a C₁₋₄ alkyl group which has been terminally substituted.

10. A transition metal complex according to claim 9 where the substituent is selected from carboxyl (and derivatives such as esters), optionally substituted amino, optionally substituted heterocyclyl, optionally substituted heteroaryl, and optionally substituted sulfonyl.

11. A transition metal complex according to claim 10 where the optionally substituted amino group is selected from NH₂, C₁₋₄ monoalkylamino, optionally substituted monoarylalkylamino, C₁₋₄ dialkylamino, quaternary ammonium salts, optionally substituted benzoyl, optionally substituted sulfonyl, and residues of amino acids and peptides.

12. A transition metal complex according to claim 9 where the substituent is selected from

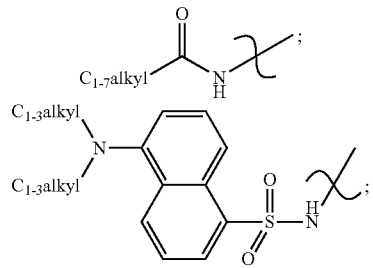

-continued

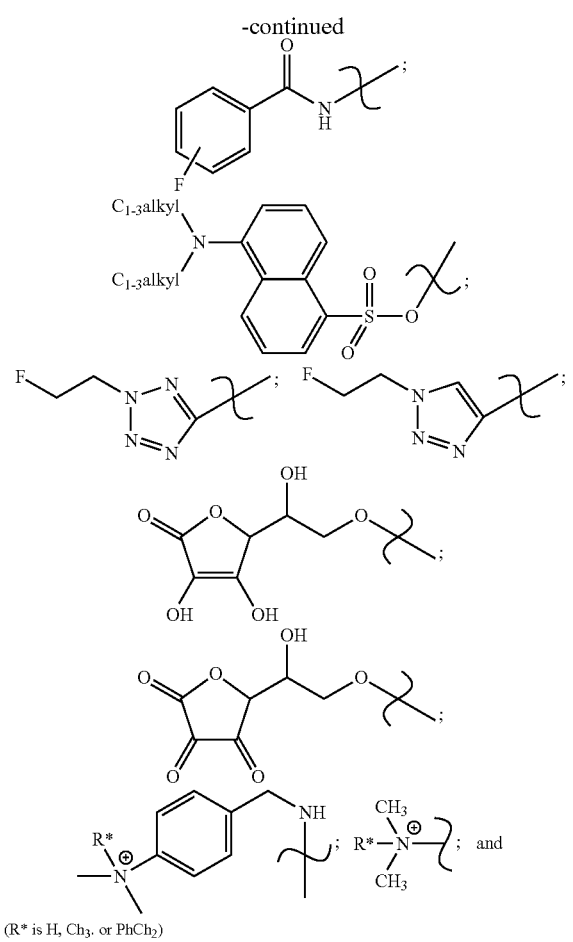

(R* is H, CH₃, or PhCh₂)

derivatives thereof.

13. A transition metal complex according to claim 1 wherein X is Pt, Pd or Ru.

14. A platinum complex of formula (I″) or a salt thereof;

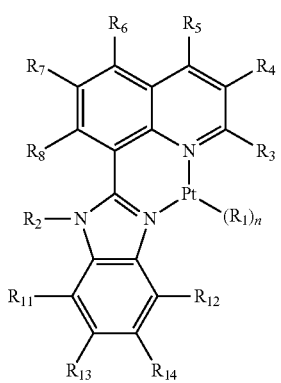

wherein:
n is an integer of 2 or 4;
each $R_1$ is independently selected from halogen, NR'R″R‴ (where each of R', R″, and R‴ is independently selected from hydrogen, alkyl, cycloalkyl, aryl, heteroaryl, heterocycyl and oxyacyl), optionally substituted acyloxy, optionally substituted alkoxy, SR'R″ (where each of R' and R″ is independently selected from hydrogen, alkyl, cycloalkyl, aryl, heteroaryl, heterocycyl and oxyacyl), optionally substituted heteroaryl, optionally substituted carbohydrate, or any two $R_1$ form a malonate, oxalate or glycolate;

$R_2$ is selected from optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and wherein each $R_3$-$R_8$ and $R_{11}$-$R_{14}$ independently represents H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy.

15. A platinum complex according to claim 14 wherein $R_2$ is a substitutent group selected from optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl.

16. A platinum complex according to claim 15 wherein $R_2$ is an optionally substituted alkyl.

17. A platinum complex according to claim 15 wherein $R_2$ is a substituted $C_{1-7}$ alkyl.

18. A platinum complex according to claim 16 wherein $R_2$ is a $C_{1-4}$ alkyl group which has been terminally substituted.

19. A platinum complex according to claim 16 where the substituent is selected from carboxyl (and derivatives such as esters), optionally substituted amino, optionally substituted heterocyclyl, optionally substituted heteroaryl, and optionally substituted sulfonyl.

20. A platinum complex according to claim 19 where the optionally substituted amino group is selected from $NH_2$, $C_{1-4}$ monoalkylamino, optionally substituted monoarylalkylamino, $C_{1-4}$ dialkylamino, quaternary ammonium salts, optionally substituted benzoyl, optionally substituted sulfonyl, and residues of amino acids and peptides.

21. A platinum complex according to claim 19 wherein the substituent is selected from

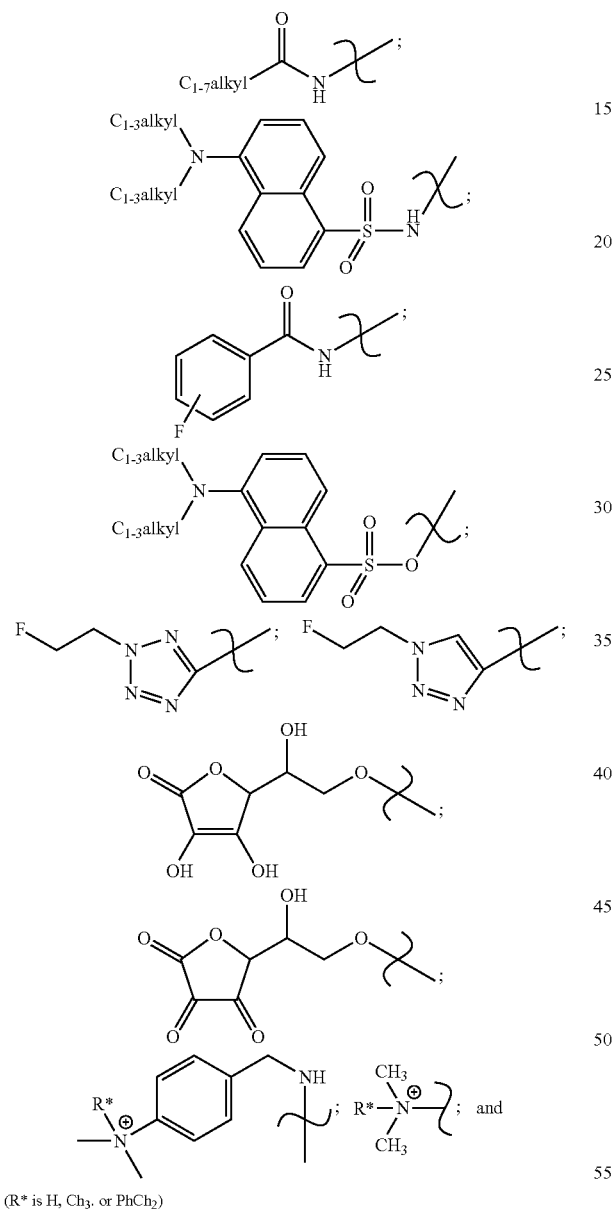

(R* is H, CH$_3$, or PhCH$_2$)

derivatives thereof.

22. A platinum complex according to claim 14 where n=2.

23. A platinum complex according to claim 14 where n=4.

24. A platinum complex according to claim 14 where each $R_1$ is chloro.

25. A platinum complex according to claim 14 wherein n=2 or n=4 and each $R_1$ together with the Pt atom represent

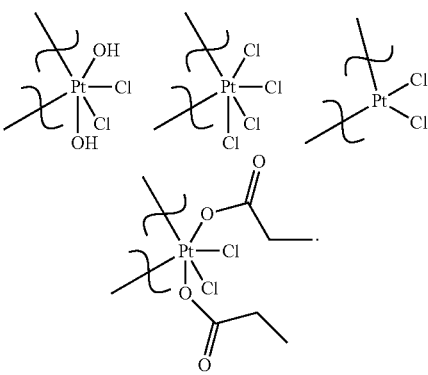

26. A method for treating Alzheimer disease including the step of administering to a patient in need thereof a transition metal complex of formula (I) or a pharmaceutically acceptable salt thereof;

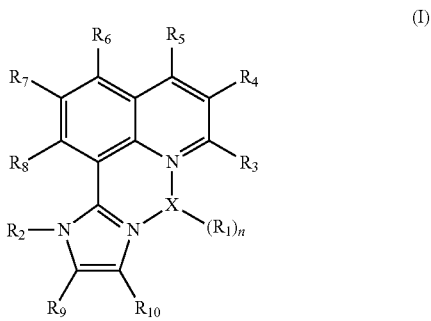

(I)

wherein:
X is selected from a transition metal consisting of Pt, Tc, Pd, Mn, Fe, Co, Ni, Ru, Cd, Au, Re, Rh and Hg;
n is an integer from 2 to 6;
each $R_1$ is independently selected from halogen, NR'R"R'" (where each of R', R", and R'" is independently selected from hydrogen, alkyl, cycloalkyl, aryl, heteroaryl, heterocycyl and oxyacyl), optionally substituted acyloxy, optionally substituted alkoxy, SR'R" (where each of R' and R" is independently selected from hydrogen, alkyl, cycloalkyl, aryl, heteroaryl, heterocycyl and oxyacyl), optionally substituted heteroaryl, optionally substituted carbohydrate, or any two $R_1$ form a malonate, oxalate or glycolate;
$R_2$ is selected from optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and
wherein each $R_3$-$R_{10}$ independently represents H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or $R_9$ and $R_{10}$ together form an optionally substituted aryl, optionally substituted heteroaryl, or optionally substituted cycloalkenyl.

27. A method of diagnosing Alzheimer disease comprising:

(i) administering a detectable quantity of a transition metal complex of formula (I) or a salt thereof to a patient;

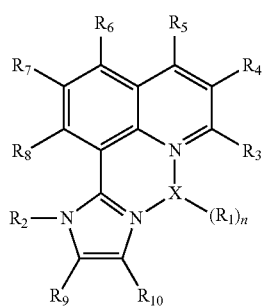

(I)

wherein:

X is selected from a transition metal consisting of Pt, Tc, Pd, Mn, Fe, Co, Ni, Ru, Cd, Au, Re, Rh and Hg;

n is an integer from 2 to 6;

each $R_1$ is independently selected from halogen, NR'R''R''' (where each of R', R'', and R''' is independently selected from hydrogen, alkyl, cycloalkyl, aryl, heteroaryl, heterocycyl and oxyacyl), optionally substituted acyloxy, optionally substituted alkoxy, SR'R'' (where each of R' and R'' is independently selected from hydrogen, alkyl, cycloalkyl, aryl, heteroaryl, heterocycyl and oxyacyl), optionally substituted heteroaryl, optionally substituted carbohydrate, or any two $R_1$ form a malonate, oxalate or glycolate;

$R_2$ is selected from optionally substituted alkyl, optionally substituted alkenyl, optionally substituted alkynyl, optionally substituted aryl, optionally substituted oxyacyl, optionally substituted acyl, optionally substituted aminoacyl, optionally substituted oxythioacyl, optionally substituted sulfinyl, optionally substituted sulfonyl, optionally substituted oxythioacyloxy, optionally substituted amino, optionally substituted aminothioacyl, optionally substituted carbohydrate, and optionally substituted thioacyl; and wherein each $R^3$-$R^{10}$ independently represents H, carboxyl, cyano, dihalomethoxy, halogen, hydroxy, nitro, pentahaloethyl, phosphono, phosphorylamino, phosphinyl, thio, sulfinyl, sulfonyl, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or $R_9$ and $R_{10}$ together form an optionally substituted aryl, optionally substituted heteroaryl, or optionally substituted cycloalkenyl; and (ii) detecting the binding of the transition metal complex to an amyloid deposit in said patient;

wherein one of $R_1$-$R_{10}$ or a substituent of an aryl, heteroaryl, or cycloalkenyl group when $R_9$ and $R_{10}$ together form a substituted aryl, substituted heteroaryl, or substituted cycloalkenyl is or comprises a group consisting of $^{131}I$, $^{123}I$, $^{76}Br$, $^{75}Br$, $^{18}F$, $^{19}F$, or a fluorescent moiety.

28. A method of diagnosing Alzheimer disease comprising:

(i) administering a detectable quantity of a transition metal complex according to claim 3 or claim 14 or a salt thereof to a patient, and (ii) detecting the binding of the transition metal complex to an amyloid deposit in said patient, wherein the transition metal complex or salt thereof is characterised with at least one label consisting of $^{131}I$, $^{123}I$, $^{76}Br$, $^{75}Br$, $^{18}F$, $^{19}F$, or a fluorescent moiety.

29. A transition metal complex selected from the following:
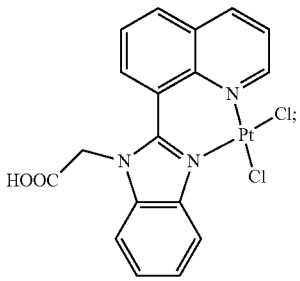
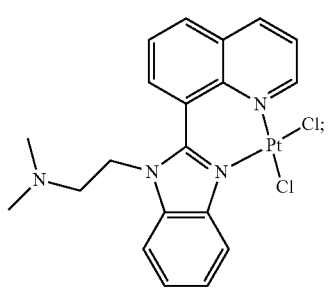
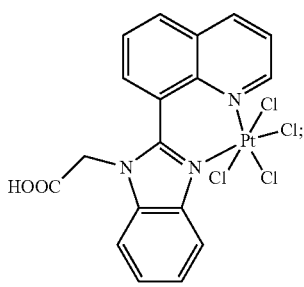
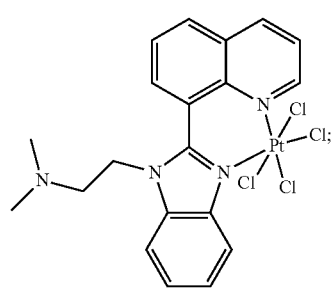
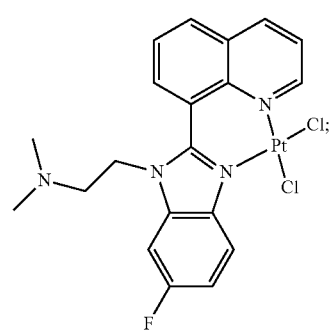
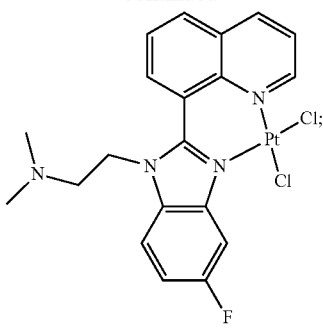
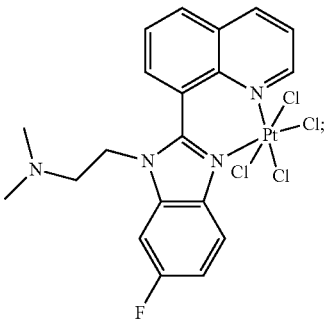
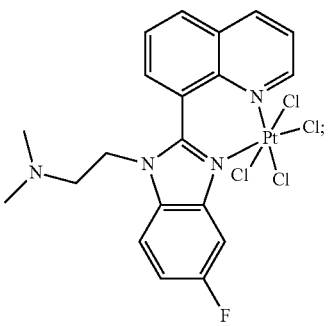
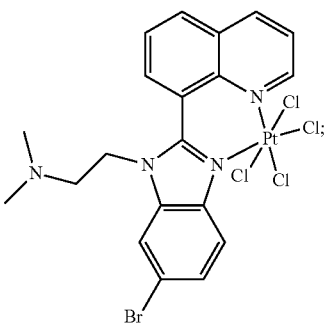
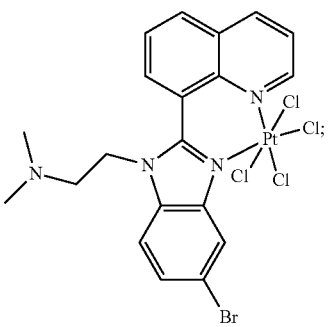

65
-continued
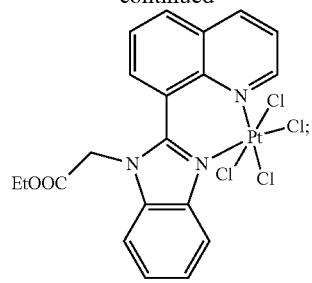
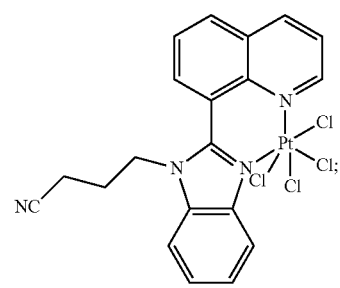
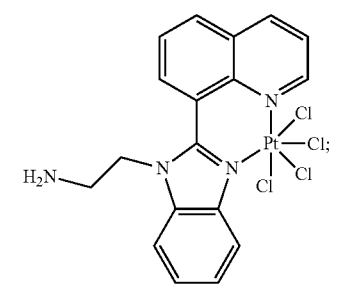
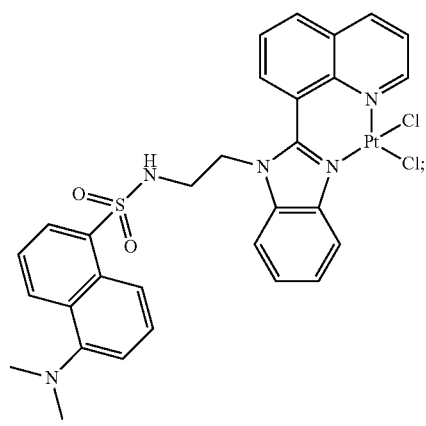
66
-continued
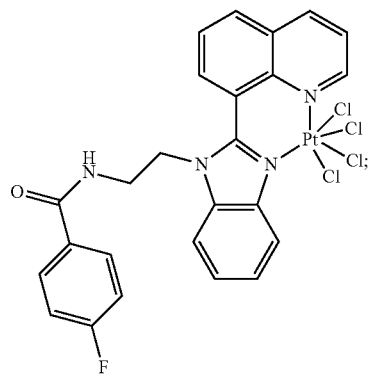
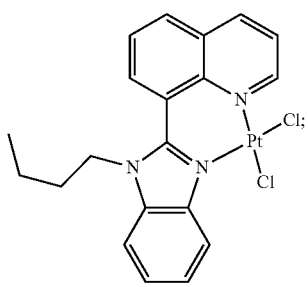
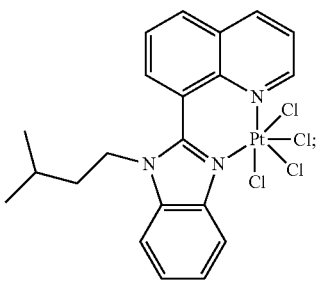
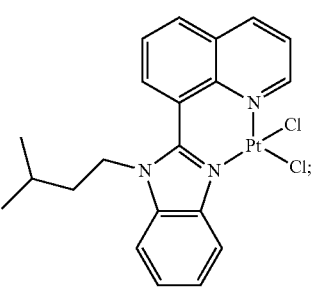

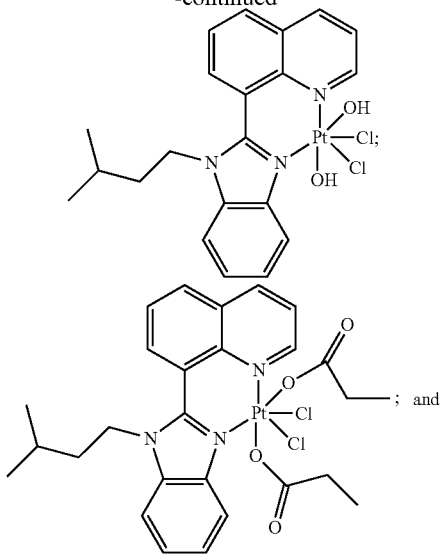
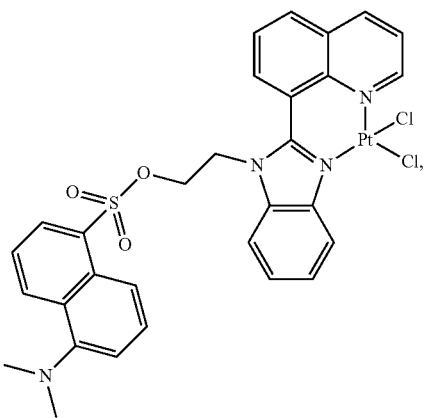
or a salt thereof.
* * * * *

UNITED STATES PATENT AND TRADEMARK OFFICE
CERTIFICATE OF CORRECTION

PATENT NO. : 8,389,506 B2
APPLICATION NO. : 12/746382
DATED : March 5, 2013
INVENTOR(S) : Barnham et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 404 days.

Signed and Sealed this
Tenth Day of September, 2013

Teresa Stanek Rea
*Acting Director of the United States Patent and Trademark Office*